United States Patent
Dong et al.

(10) Patent No.: US 9,895,363 B2
(45) Date of Patent: Feb. 20, 2018

(54) METHODS FOR MODULATING FUNCTION OF PROLIFERATING CELL NUCLEAR ANTIGEN (PCNA) AND TREATING CANCER WITH PCNA-TARGETING COMPOUNDS

(75) Inventors: Zhongyun Dong, Cincinnati, OH (US); Matthew Wortman, Fort Wright, KY (US); Zonqing Tan, Cincinnati, OH (US); Kelsey Dillehay, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 273 days.

(21) Appl. No.: 13/821,789

(22) PCT Filed: Sep. 8, 2011

(86) PCT No.: PCT/US2011/050867
§ 371 (c)(1),
(2), (4) Date: Sep. 26, 2013

(87) PCT Pub. No.: WO2012/033938
PCT Pub. Date: Mar. 15, 2012

(65) Prior Publication Data
US 2014/0018385 A1    Jan. 16, 2014

Related U.S. Application Data

(60) Provisional application No. 61/380,733, filed on Sep. 8, 2010.

(51) Int. Cl.
| | |
|---|---|
| *A61K 45/06* | (2006.01) |
| *A61K 31/4704* | (2006.01) |
| *A61K 31/166* | (2006.01) |
| *A61K 31/382* | (2006.01) |
| *A61K 31/415* | (2006.01) |
| *A61K 33/24* | (2006.01) |
| *A61K 31/381* | (2006.01) |

(52) U.S. Cl.
CPC ........ *A61K 31/4704* (2013.01); *A61K 31/166* (2013.01); *A61K 31/381* (2013.01); *A61K 31/382* (2013.01); *A61K 31/415* (2013.01); *A61K 33/24* (2013.01)

(58) Field of Classification Search
None
See application file for complete search history.

(56) References Cited

U.S. PATENT DOCUMENTS

| | | | |
|---|---|---|---|
| 6,277,844 B1 * | 8/2001 | Spector et al. | 514/215 |
| 2006/0235034 A1 * | 10/2006 | Neamati | C07C 243/32 514/267 |
| 2008/0167385 A1 | 7/2008 | Kontopidis et al. | |
| 2008/0280896 A1 * | 11/2008 | Attardo | A61K 31/4025 514/230.5 |
| 2009/0304805 A1 * | 12/2009 | Desai et al. | 424/499 |
| 2010/0120781 A1 | 5/2010 | Neamati | |

FOREIGN PATENT DOCUMENTS

| | | | | |
|---|---|---|---|---|
| WO | 2008014307 | | 1/2008 | |
| WO | WO2013071001 A1 * | | 5/2013 | A61K 31/44 |

OTHER PUBLICATIONS

Ukrainets et al., Chemistry of Heterocyclic Compounds, vol. 44, No. 11, 2008, p. 1347-1354.*
Narasimhan et al., Acta Pharmaceutica Sciencia 52: 169-180 (2010).*
Zhao et al., Zhongguo Weishengtaixue Zazhi (2010), 22, (4), 346-349.*
Gadgul, A. et al., Research Journal of Pharmacy and Technology Year : 2010, vol. 3, Issue : 4 First page : ( 1023) Last page : ( 1028) Print ISSN : 0974-3618. Online ISSN : 0974-360X.*
Caballero et al, "Docking and Quantitative Structure-Activity Relationship Studies for Sulfonyl Hydrazides as Inhibitors of Cytosolic Human Branched-Chain Amino Acid Aminotransferase." Mol Divers. 2009, 13(4):493-500.
Zhang et al, "Tumor-Infiltraing Macrophages Involved in Suppressing Growth and Metastasis of Human Prostate Cancer Cells by INF-Beta Gene Therapy in Nude Mice"; Clin. Cancer Res. 2002; 8:29:2942-51.

* cited by examiner

*Primary Examiner* — Sreeni Padmanabhan
*Assistant Examiner* — Jeanmarie Calvillo
(74) *Attorney, Agent, or Firm* — Dinsmore & Shohl LLP

(57) ABSTRACT

Pharmaceutical compositions and methods for inhibiting cell growth, modulating function of PCNA, treating prostate cancer, and enhancing PCNA trimer formation are disclosed. The methods include administering an effective amount of a compound of Formula (I):

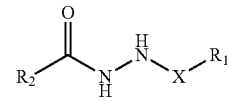

(a representative image), or an effective amount of a specific compound of Formula (II):

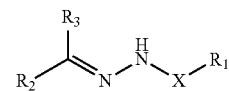

(a representative image).

31 Claims, 22 Drawing Sheets

METHODS FOR MODULATING FUNCTION OF PROLIFERATING CELL NUCLEAR ANTIGEN (PCNA) AND TREATING CANCER WITH PCNA-TARGETING COMPOUNDS

This application claims priority under 35 U.S.C. § 119 to U.S. Provisional Application Ser. No. 61/380,733, filed Sep. 8, 2010, the contents of which are hereby incorporated by reference in their entirety.

The present disclosure relates to pharmaceutical compositions and methods for inhibiting growth of a cell, modulating function of proliferating cell nuclear antigen in a cell, treating prostate cancer, and enhancing trimer formation of proliferating cell nuclear antigen.

Proliferating cell nuclear antigen (hereinafter "PCNA") is a protein that is ubiquitously expressed in all types of eukaryotic cells. PCNA plays a crucial role in many vital processes; for example, PCNA is involved in DNA replication, DNA repair, chromatin remodeling, sister-chromatid cohesion, cell-cycle control and regulation, and chromatin assembly and maintenance in eukaryotic cells. Functional PCNA is a homotrimer with a ring structure, in which three monomers are joined together in an anti-parallel tail to head interaction through amide-to-carboxyl hydrogen bonds between two β sheets, a small hydrophobic core, and putative ion pairs. Functional PCNA serves as a sliding clamp, encircling double-stranded DNA. Functional PCNA performs vital cellular functions by interacting with a variety of partner proteins, including: DNA polymerase δ, DNA polymerase ε, and replication factor C for DNA replication; DNMT1, HDAC1, and p300 for chromatin assembly and gene regulation; DNA mismatch repair protein Msh3 and Msh6 for DNA repair; p21 (CIP1/WAF1), p15 cyclin D1, and CDK2 for cell cycle control; and ESCO1 and ESCO2 for sister-chromatid cohesion. Accordingly, functional PCNA is absolutely required for cell growth.

PCNA is synthesized in all stages of the cell cycle. However, the rate of synthesis of PCNA is elevated by about two to three fold in early S phase to support cell cycle progression. The majority of PCNA in all phases of the cell cycle is present in the free-form in the nucleus while approximately 20% to 30% of PCNA in the S phase of the cell cycle is associated with chromatin involving DNA replication. PCNA is under tight posttranslational regulation, including ubiquitination, phosphorylation, acetylation, and methylation.

PCNA gene deregulation and posttranslational modulation are significant hallmarks of malignant cells. Tumor cells, regardless of their origins, express higher levels of PCNA. Accordingly, PCNA is an excellent indicator for cancer diagnosis, prognosis, and therapeutic response in head and neck tumors, breast cancer, and prostate cancer. For example, a positive correlation exists between the expression of PCNA and several pathological indices associated with prostate cancer; specifically, a positive correlation exists between the expression of PCNA and Gleason score, pathological stages, and prostatic specific antigen (hereinafter "PSA") in human prostate cancer. Moreover, PCNA is overexpressed in locally advanced and biologically progressive prostate cancer and has significant prognostic value for disease-free survival. For example, PCNA labeling index (hereinafter "PCNA LI") was significantly higher in patients with elevated PSA levels, advanced clinical stage disease, and high Gleason scores. Additionally, the five-year cumulative rate of death from prostate cancer was significantly higher in patients (about 62%) with a PCNA LI of about 20 or more than those (about 4%) with a PCNA LI of less than about 20. Accordingly, there is an urgent need to alter the function of PCNA.

In 2010, prostate cancer was the most common cancer and the second most common cause of cancer death among men in the United States. While improved detection techniques have resulted in diagnosis of localized disease, metastasis still occurs in many patients prior to initial diagnosis. Accordingly, eradication of primary tumors by either surgery or radiation therapy is not curative. Since prostate cancer is insensitive to most chemotherapeutic agents, hormonal therapy is a mainstay treatment for advanced disease. However, current hormonal therapies are palliative, delaying tumor progression by an average of less than about 18 months. Accordingly, there is an urgent need to develop improved therapeutic agents for prostate cancer.

The present disclosure is based on the discovery that a compound of the Formula (I) is effective for inhibiting growth, modulating function of PCNA, treating prostate cancer, and enhancing trimer formation of PCNA. Accordingly, in one embodiment, a method for inhibiting growth of a cell is disclosed. The method includes contacting the cell with an effective amount of a compound having Formula (I) or Formula (II), provided below:

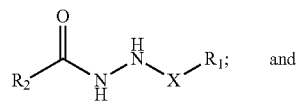

Formula (I)

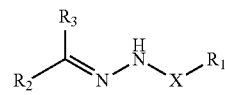

Formula (II)

wherein:

X is selected from the group consisting of carbonyl and

$R_1$ is selected from the group consisting of

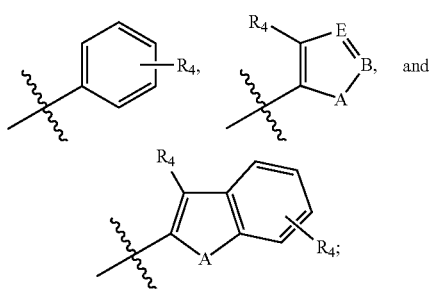

A is selected from the group consisting of —$NR_4$ and S;

B and E are independently selected from the group consisting of —$CR_4$ and —$NR_4$;

each $R_4$ is independently selected from the group consisting of H, halo, nitro, cyano, hydroxyl, carbonyl, a $C_1$-$C_4$ alkyl, —$OR_3$, and —$N(R_3)_2$;

$R_3$ is selected from the group consisting of H and a $C_1$-$C_4$ alkyl; and $R_2$ is selected from the group consisting of

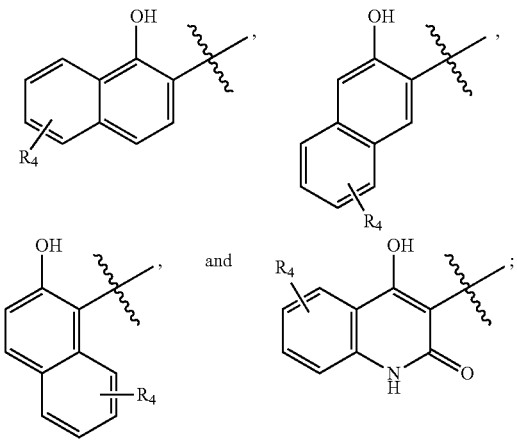

and tautomers thereof.

In another embodiment, a method for modulating function of PCNA in a cell is disclosed. The method includes contacting the cell with an effective amount of a compound of Formula (I) or Formula (II).

In yet another embodiment, a method for treating prostate cancer in a subject in need thereof is disclosed. The method includes administering an effective amount of a compound of Formula (I) or Formula (II) to the subject.

In another embodiment, a pharmaceutical composition for administration to a subject for the treatment of prostate cancer is disclosed. The pharmaceutical composition includes a compound of Formula (I) or Formula (II).

In another embodiment, a method for enhancing trimer formation of PCNA is disclosed. The method includes contacting the PCNA with an effective amount of a compound of Formula (I) or Formula (II).

These and other features and advantages of these and other various embodiments according to the present invention will become more apparent in view of the drawings, detailed description, and claims provided herein.

The following detailed description of the embodiments of the present invention can be better understood when read in conjunction with the following drawings, where like structure is indicated with like reference numerals, and in which:

FIG. 1 is a graph of the fluorescence intensity ($\times 10^5$) of PC-3 cells without or with PCNA-I1 (0.5 µM for 24 H) with respect to time (H);

FIG. 2 depicts the effects of PCNA-I1 on tumor and normal cells, wherein (A) is a bar graph of fluorescence intensity (530/580, $\times 10^{-4}$) of mouse lymphocytes without and with concanavalin A with respect to treatment; (B) is a graph of growth inhibition (%) of tumor cells including PC-3 cells, mouse lymphocytes without concanavalin A, and mouse lymphocytes with concanavalin A, with respect to PCNA-I1 concentration (nM); and (C) is a graph of growth inhibition (%) of normal cells including MSC, HUVEC, Mu-Lu-Endo, and Mu-Pr-Endo, and tumor PC-3 cells with respect to PCNA-I1 concentration (nM);

Figure 10:
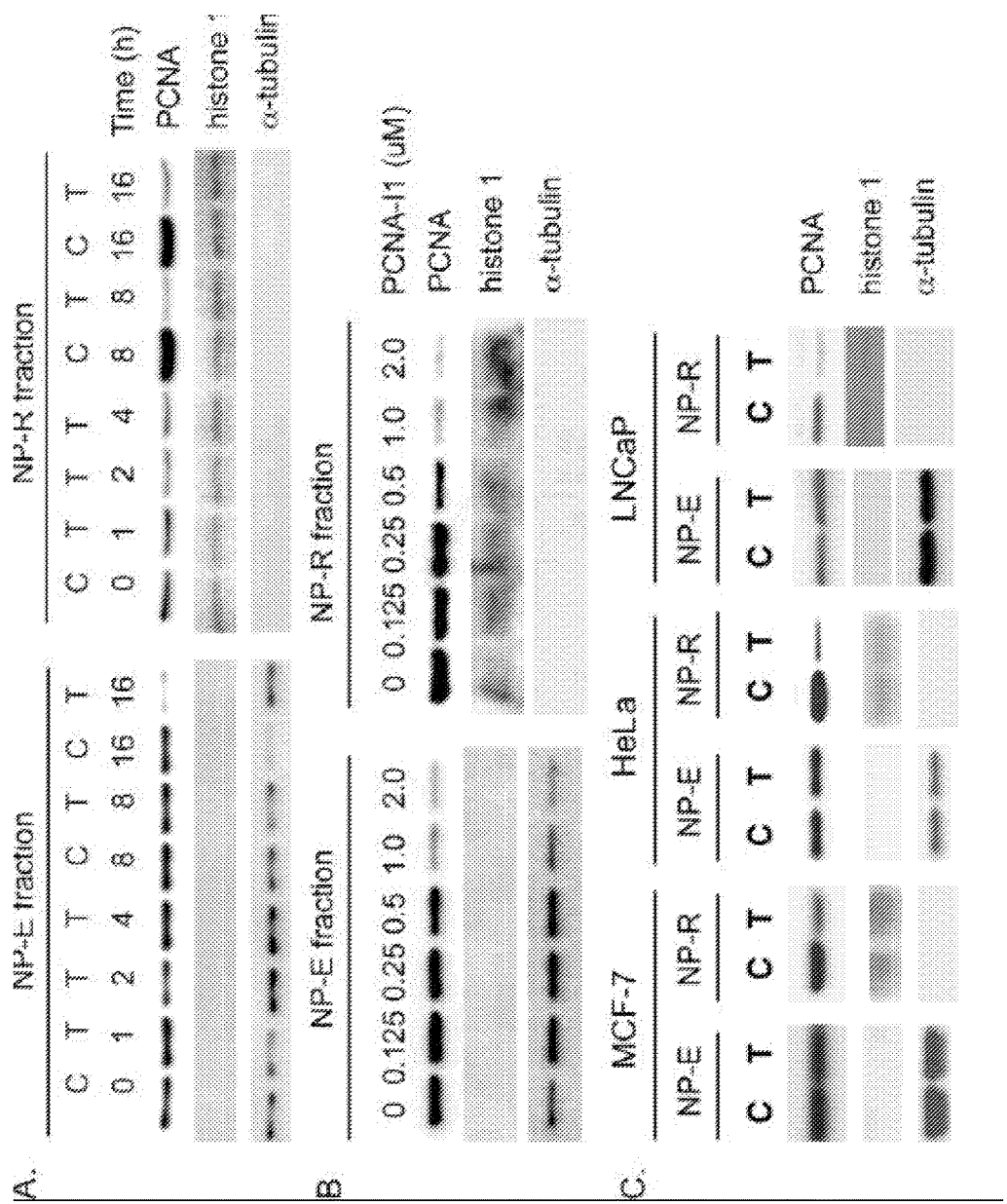
Figure 11:
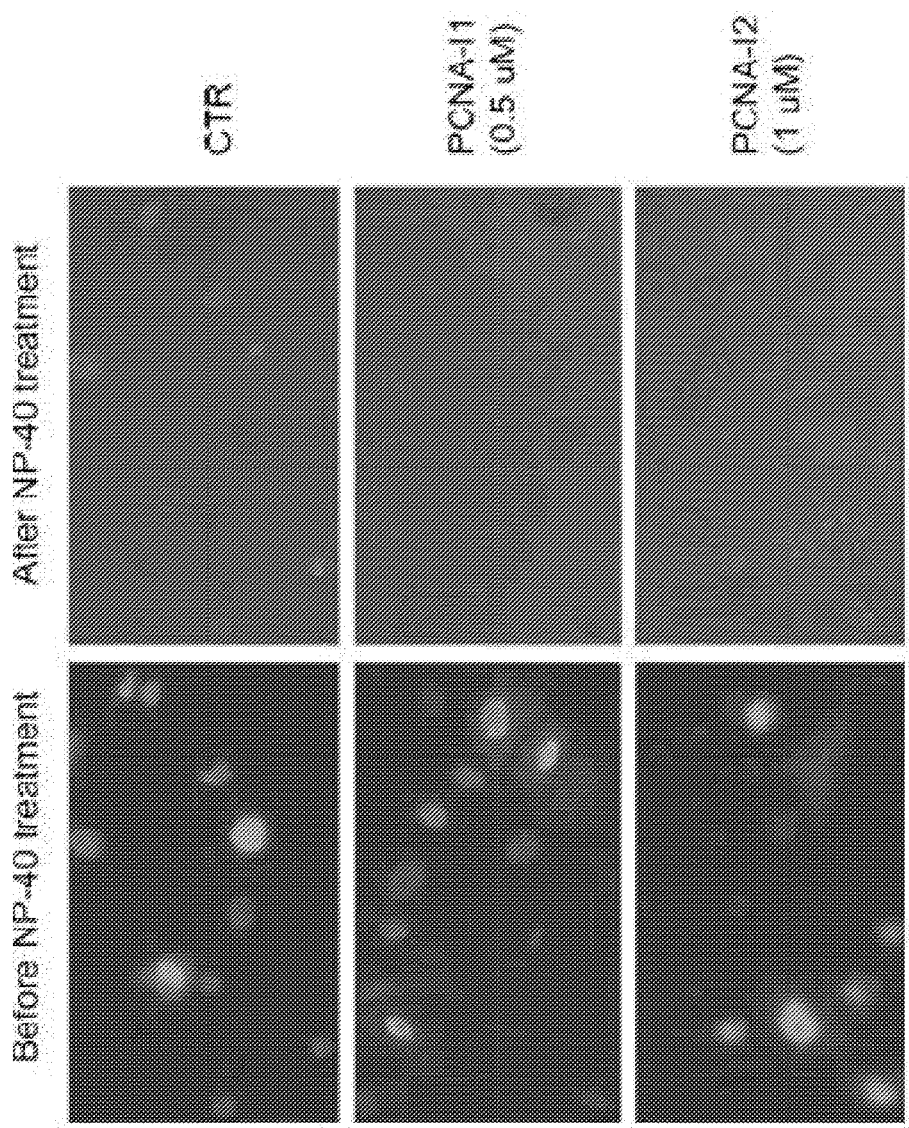
Figure 12:
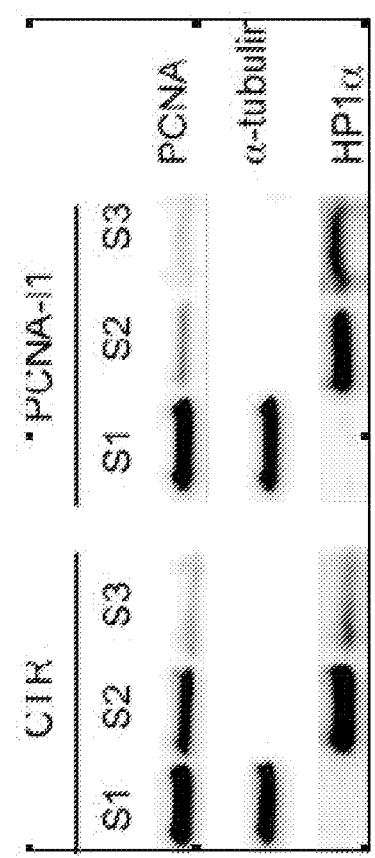
Figure 13:
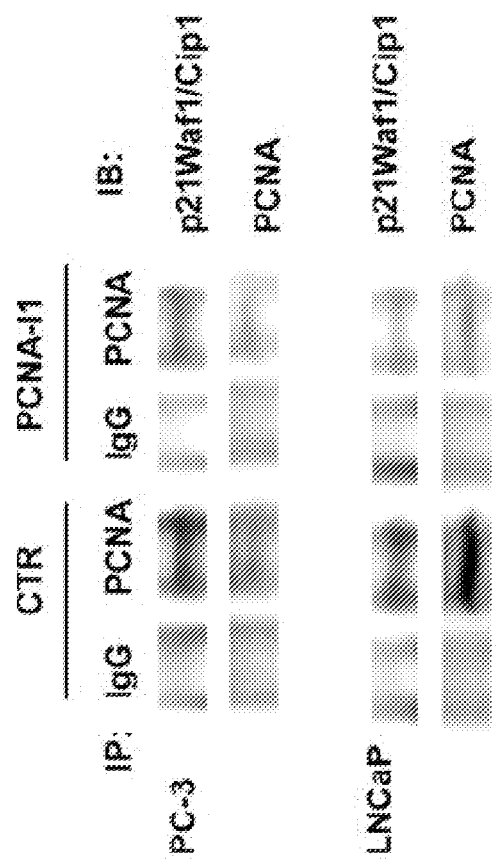
Figure 14:
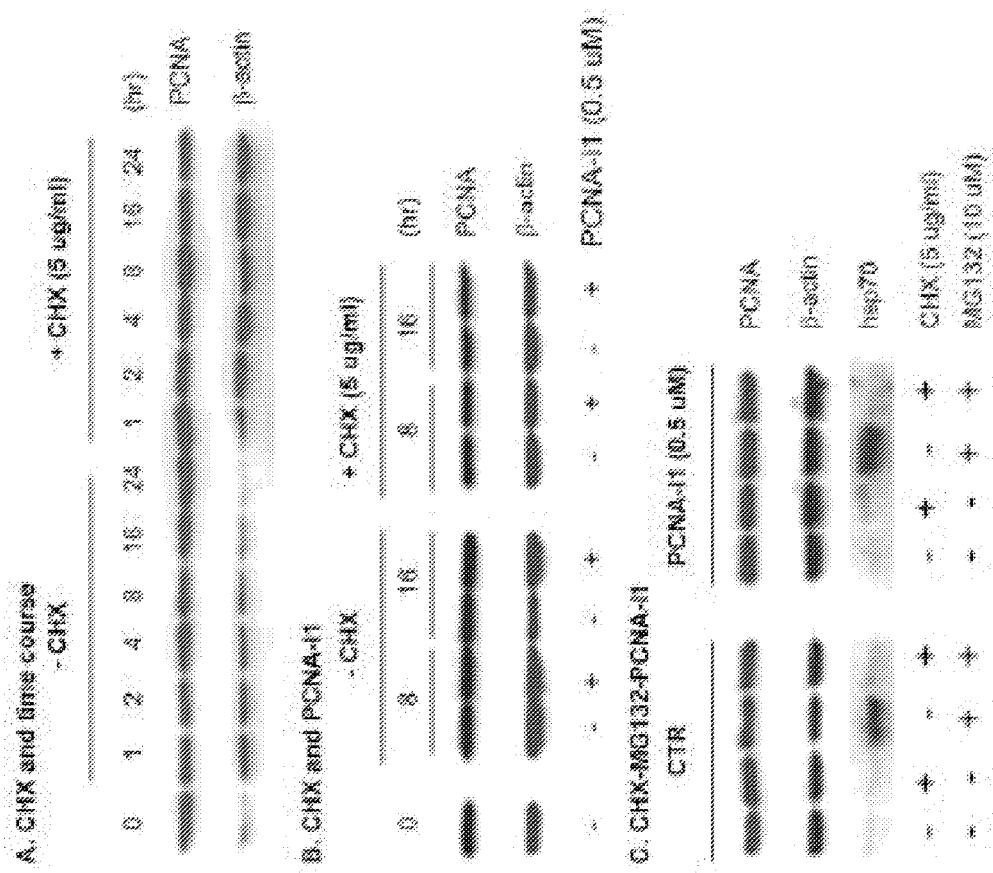
Figure 15:
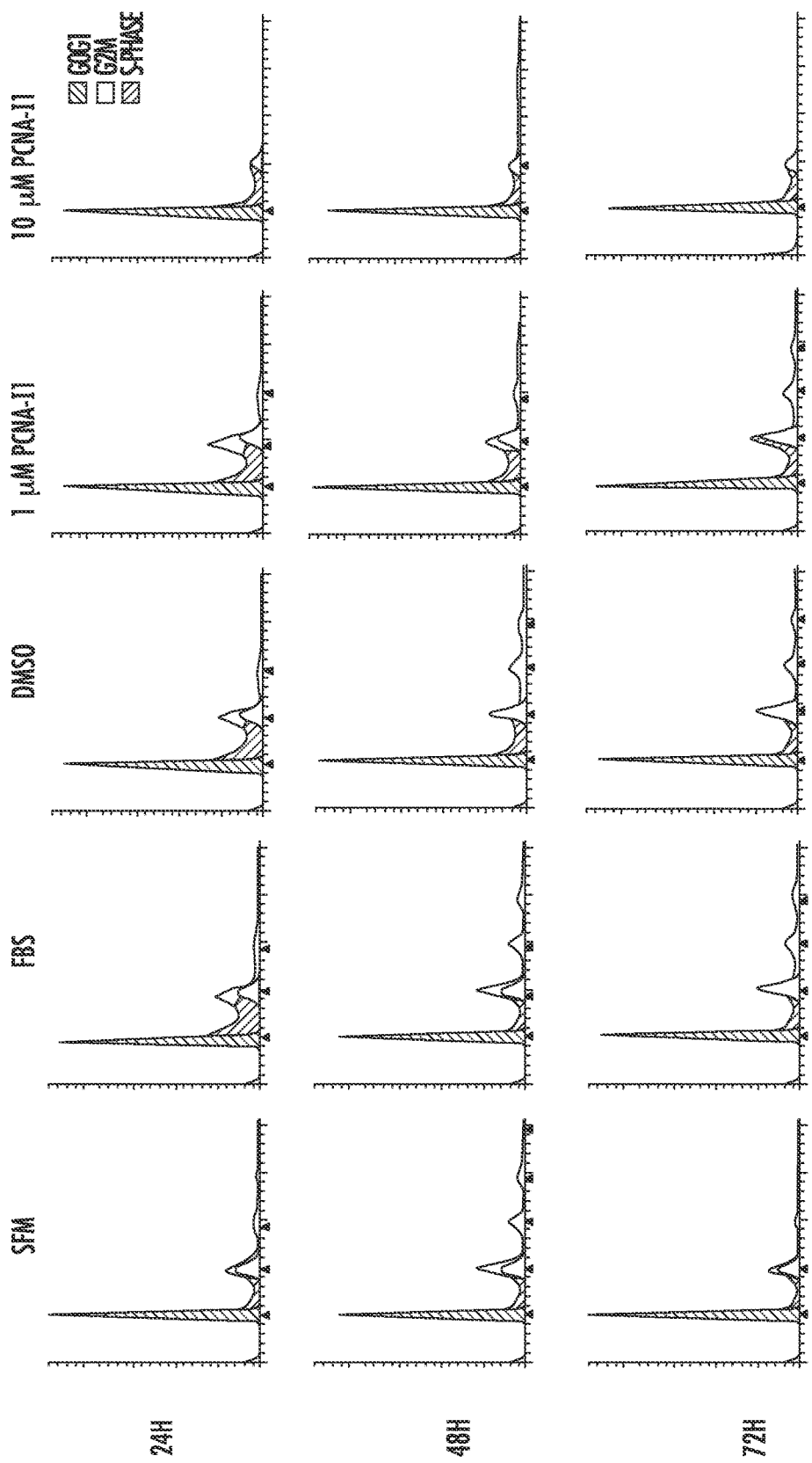
Figure 16:
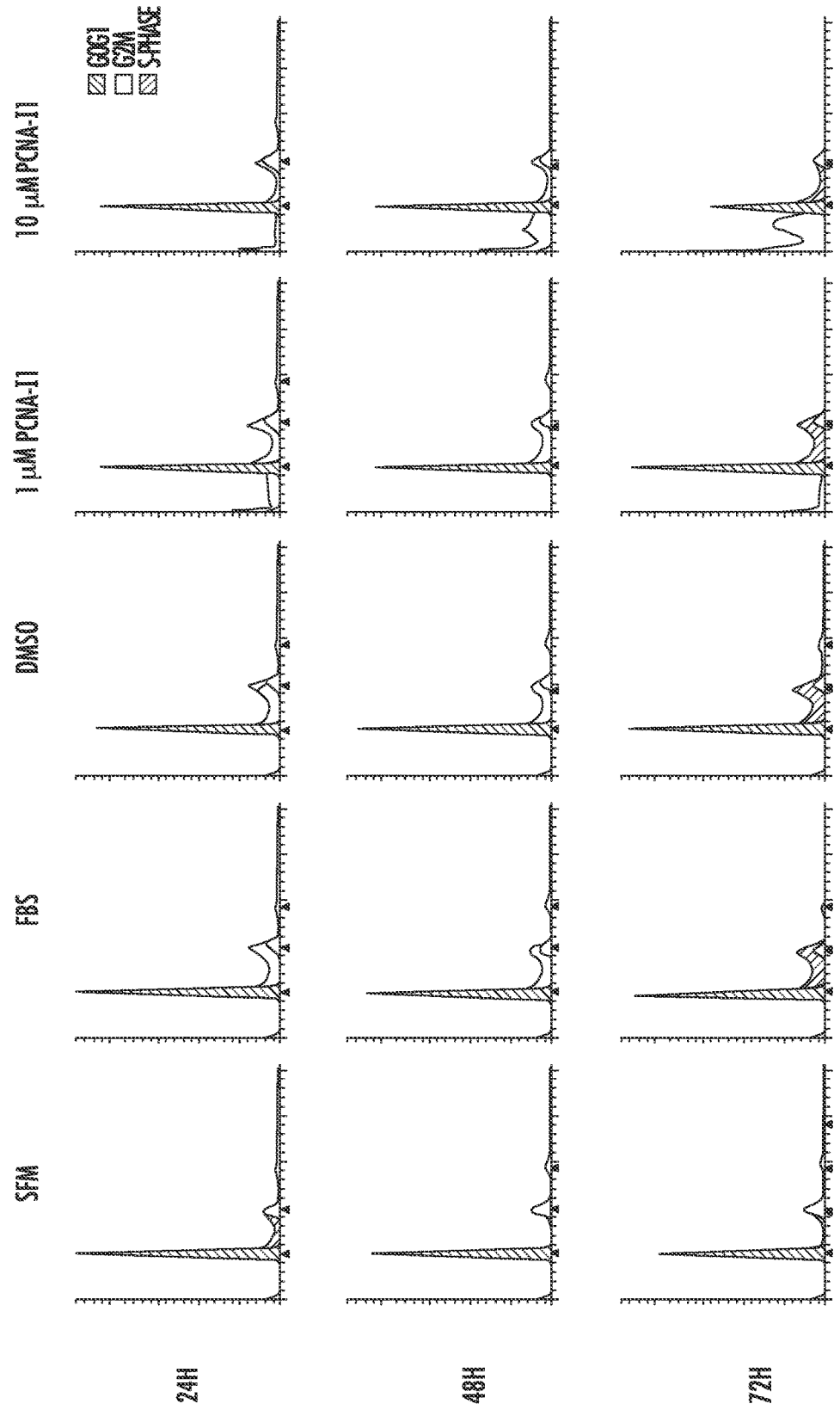
Figure 17:
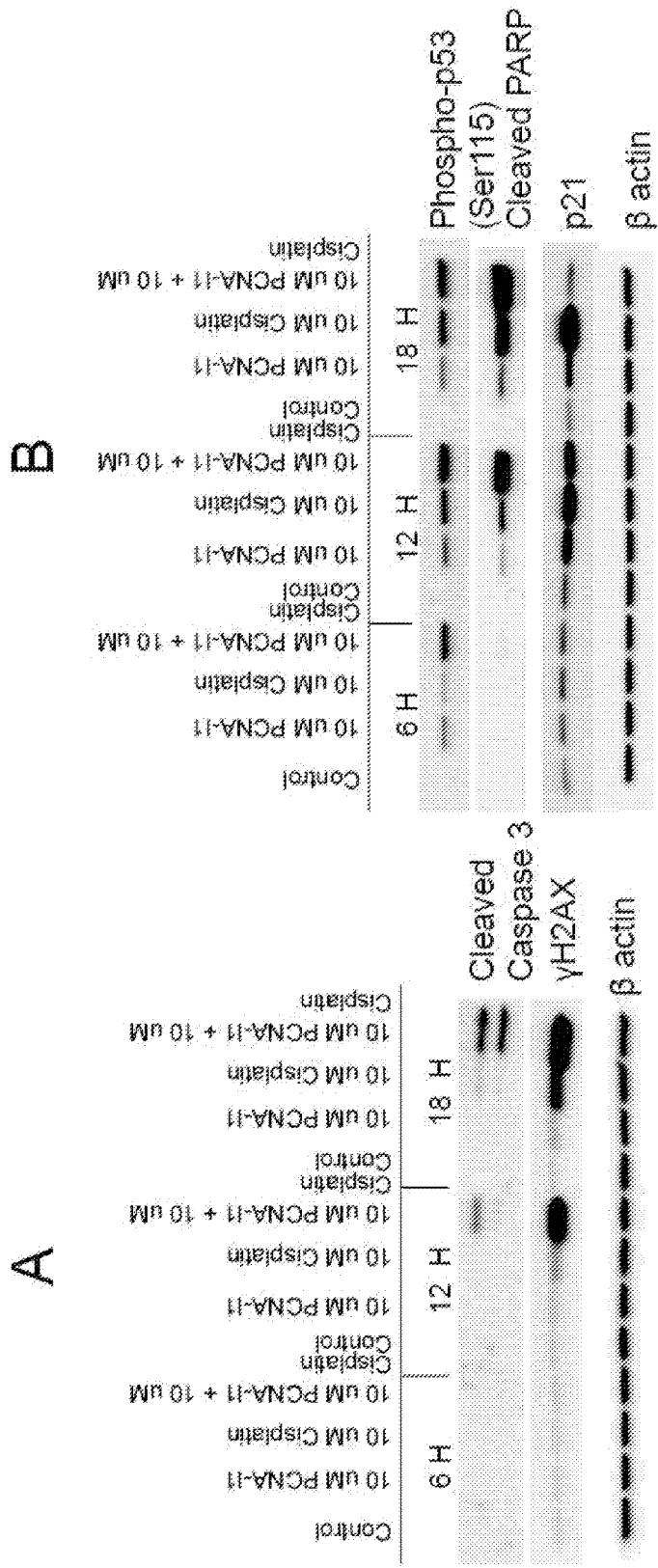
Figure 18:
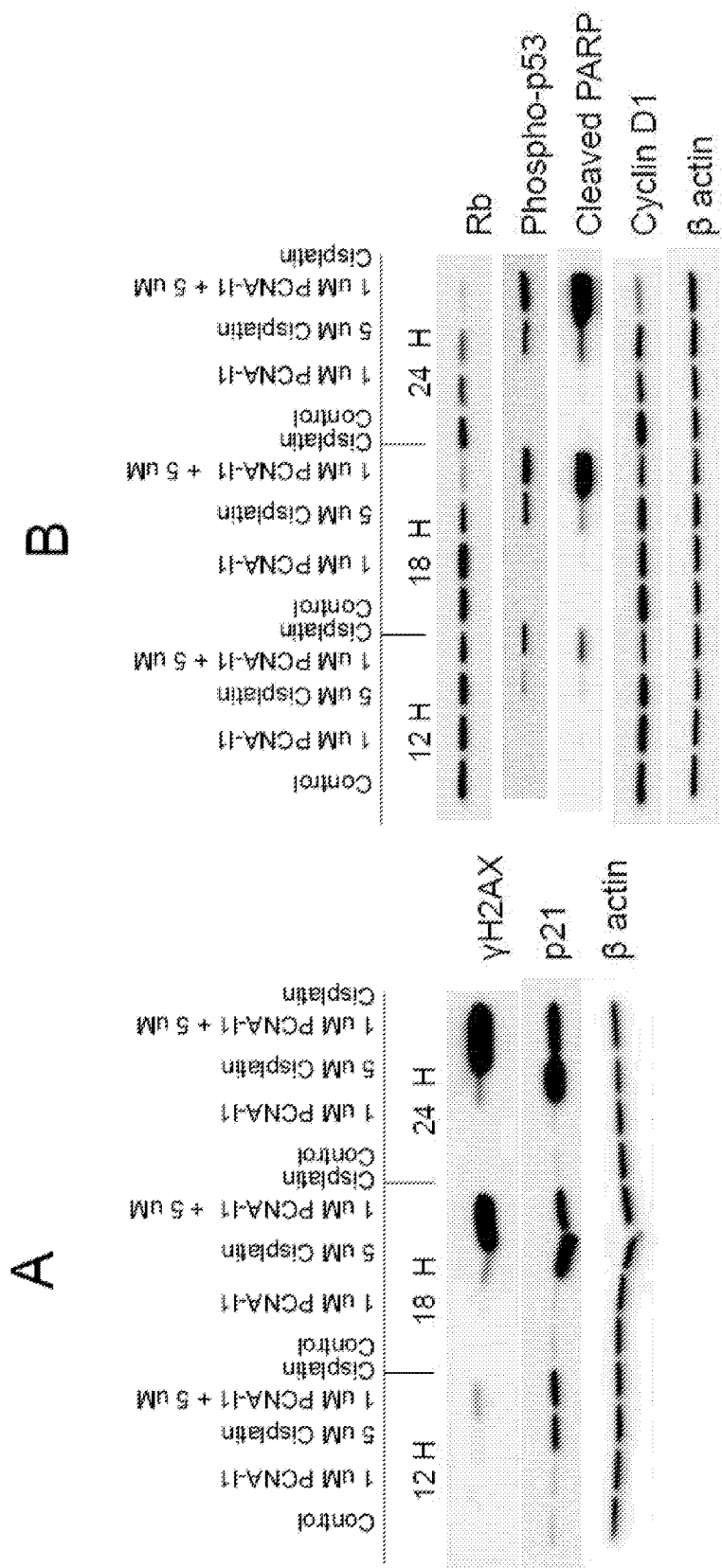
Figure 19:
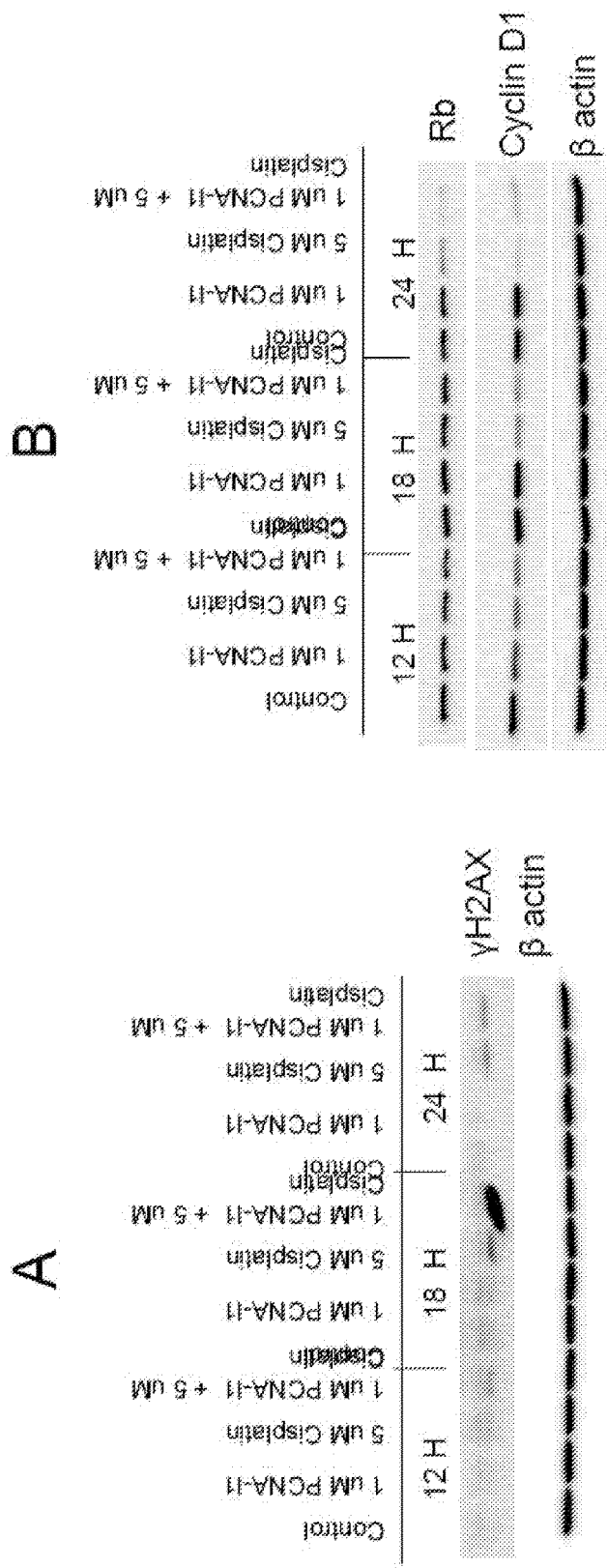
Figure 20:
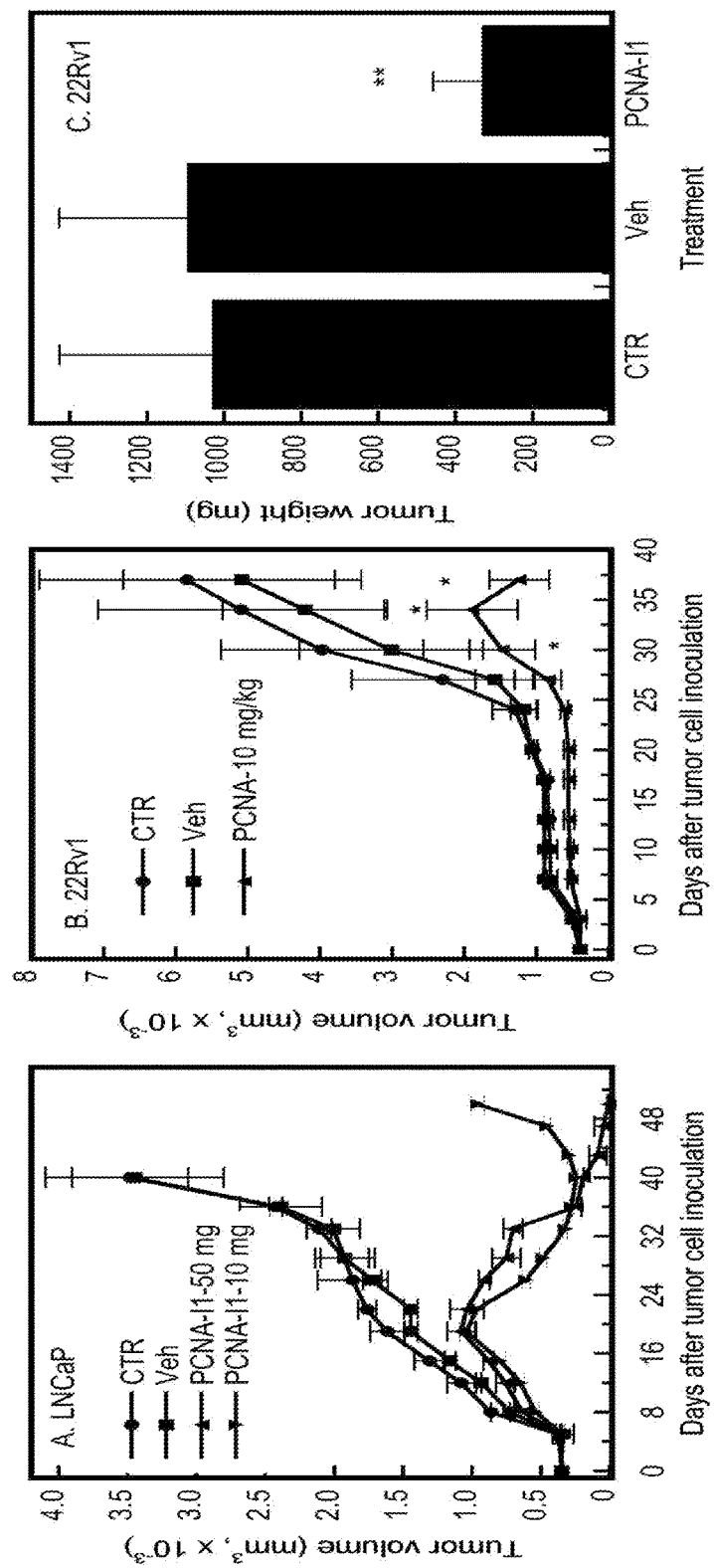
Figure 21:
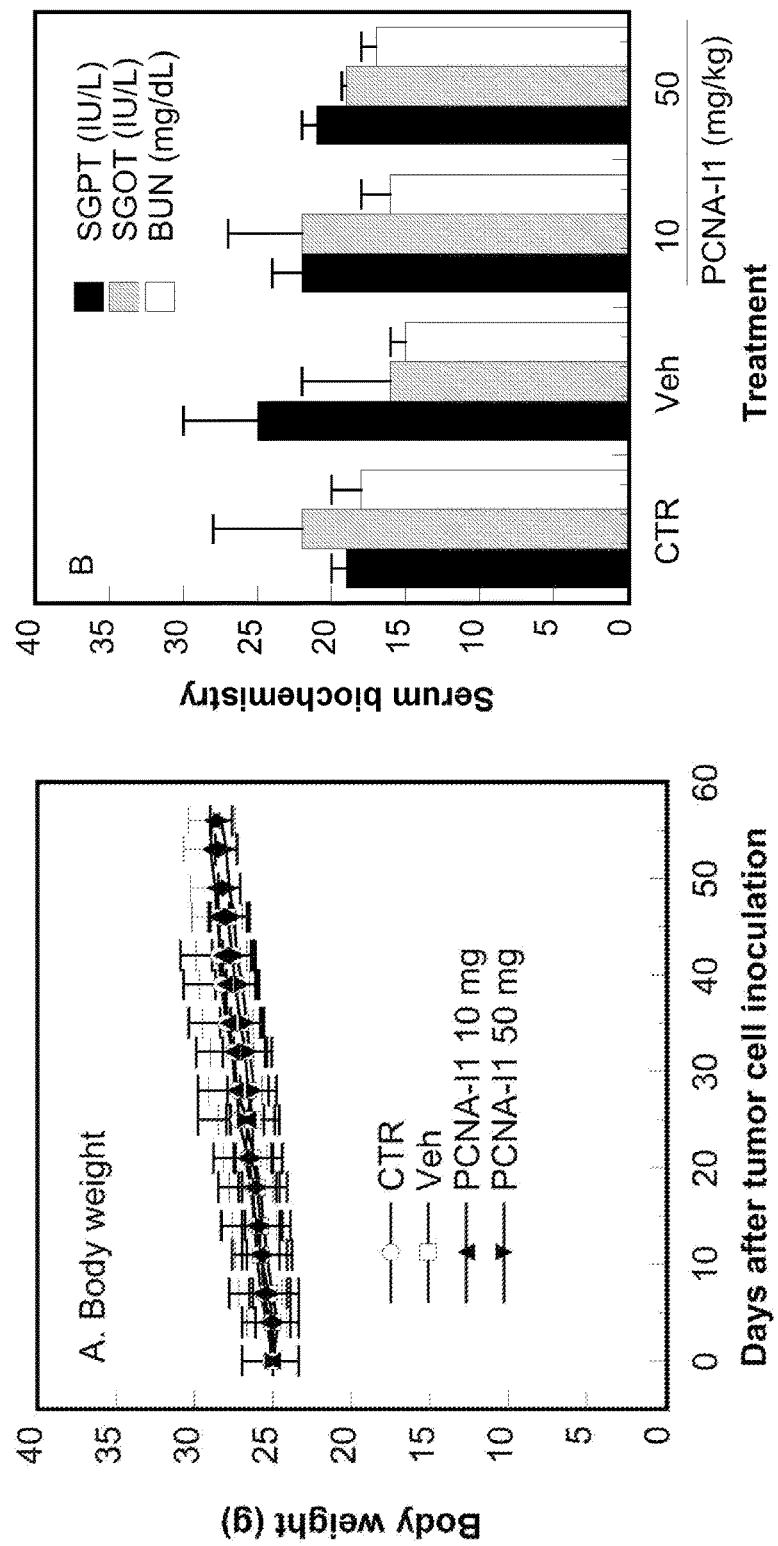
Figure 22:
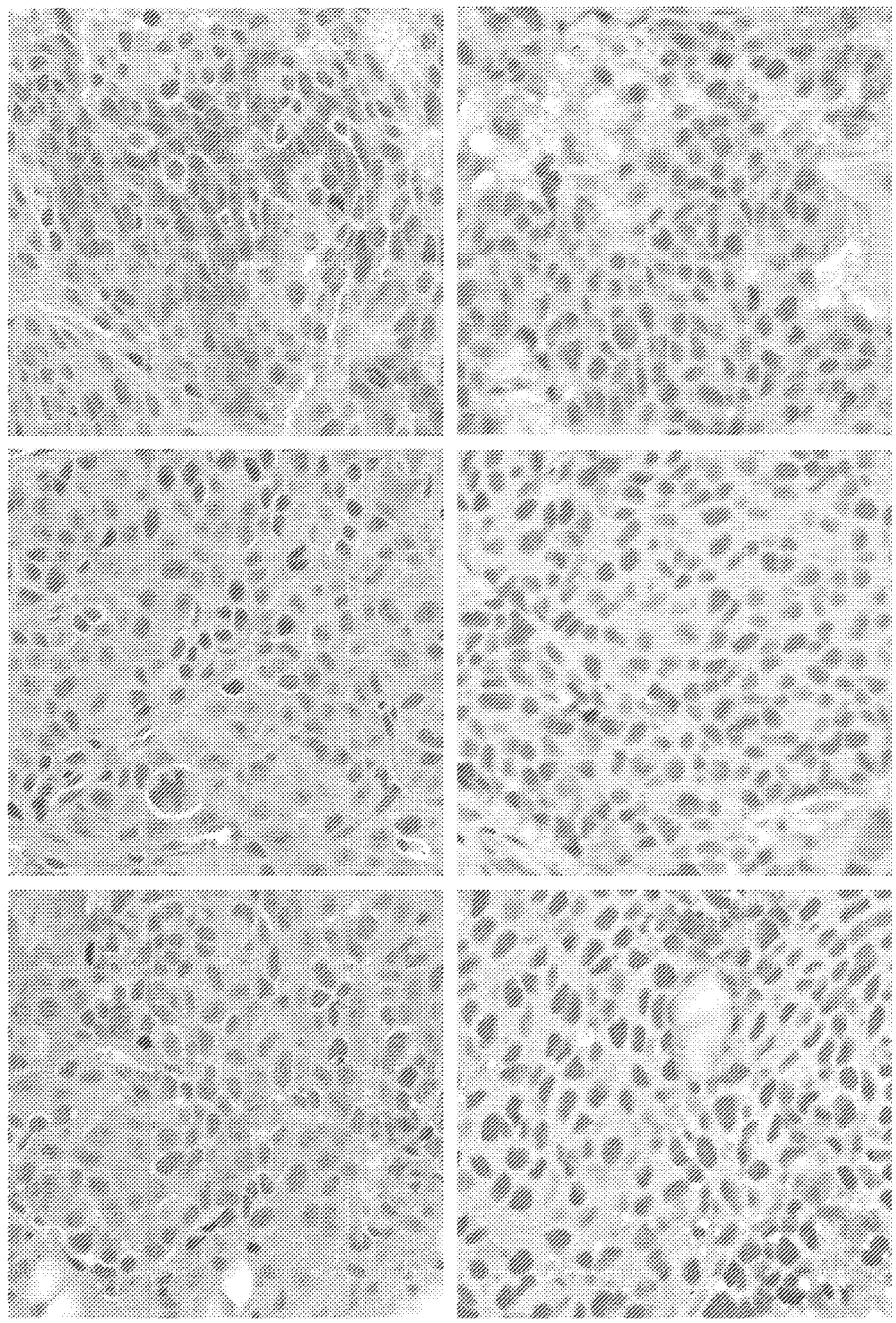

FIG. 10 is a western blot which depicts (A) PCNA in free-form (NP-E) and chromatin-associated (NP-R) fractions of PC-3 cells at various times (0 H, 1 H, 2 H, 4 H, 8 H, and 16 H) in the absence (C) or presence (T) of PCNA-I1 (0.5 µM); (B) PCNA in NP-E and NP-R fractions of PC-3 cells at various concentrations of PCNA-I1 (0 µM, 0.125 µM, 0.25 µM, 0.25 µM, 0.5 µM, 1.0 µM, and 2.0 µM); and (C) PCNA in NP-E and NP-R fractions of MCF-7, HeLa, and LNCaP cells in the absence (C) or presence (T) of PCNA-I1 (0.5 µM);

FIG. 11 is a fluorescent image of PC-3 cells transfected for 24 H with pGFP-PCNA in the absence or presence of PCNA-I1 (0.5 µM) or PCNA-I2 (1 µM) before and after treatment with NP-40 buffer B;

FIG. 12 is a western blot which depicts total (S1), euchromatin- (S2), and heterochromatin-associated (S3) PCNA in the absence (CTR) or presence (PCNA-I1) of PCNA-I1 (0.5 µM);

FIG. 13 is an immunoblot of p21Waf1/Cip1 and PCNA in PC-3 and LNCaP cells in the absence (CTR) or presence (PCNA-I1) of PCNA-I1 (0.5 µM);

FIG. 14 is an immunoblot of: (A) PCNA in PC-3 cells in the absence or presence of CHX (5 µg/mL) at 0 H, 1 H, 2 H, 4 H, 8 H, 16 H, and 24 H; (B) PCNA in PC-3 cells in the absence or presence of CHX (5 µg/mL) and PCNA-I1 (0.5 µM) at 0 H, 8 H, and 16 H; and (C) PCNA in PC-3 cells in the absence or presence of CHX (5 µg/mL), PCNA-I1 (0.5 µM), and MG132 (10 µM);

FIG. 15 is a cell cycle distribution profile of PC-3 cells in serum free medium (SFM) or in medium supplemented with 5% FBS or in DMSO in the absence or presence of PCNA-I1 (1 µM or 10 µM) at 24 H, 48 H, and 72 H;

FIG. 16 is a cell cycle distribution profile of LNCaP cells in serum free medium (SFM) or in medium supplemented with 5% FBS or in DMSO in the absence or presence of PCNA-I1 (1 µM or 10 µM) at 24 H, 48 H, and 72 H;

FIG. 17 is an immunoblot of: (A) DNA damage in LNCaP cells in the absence or presence of PCNA-I1 (10 µM) and/or cisplatin (10 µM) at 6 H, 12 H, and 18 H; and (B)

apoptosis-related proteins phospho-p53 and cleaved PARP in LNCaP cells in the absence or presence of PCNA-I1 (10 μM) and/or cisplatin (10 μM) at 6 H, 12 H, and 18 H; and FIG. 18 is an immunoblot of: (A) γH2AX and p21 in LNCaP cells in the absence or presence of PCNA-I1 (1 μM) and/or cisplatin (5 μM) at 12 H, 18 H, and 24 H; and (B) Rb, phospho-p53, and cleaved PARP in LNCaP cells in the absence or presence of PCNA-I1 (1 μM) and/or cisplatin (5 μM) at 12 H, 18 H, and 24 H;

FIG. 19 is an immunoblot of: (A) γH2AX in PC-3 cells in the absence or presence of PCNA-I1 (1 μM) and/or cisplatin (5 μM) at 12 H, 18 H, and 24 H; and (B) Rb and Cyclin D1 in LNCaP cells in the absence or presence of PCNA-I1 (1 μM) and/or cisplatin (5 μM) at 12 H, 18 H, and 24 H;

FIG. 20 depicts the therapeutic effects of PCNA-I1 in animal tumor models, including: (A) a graph of tumor volume ($mm^3$, $\times 10^{-3}$) in male nude mice implanted with LNCaP cells injected with a vehicle, PCNA-I1 (50 mg/kg), or PCNA-I1 (10 mg/kg) with respect to time (days); (B) a graph of tumor volume ($mm^3$, $\times 10^{-3}$) in male nude mice implanted with 22Rv1 cells injected with a vehicle, and/or PCNA-I1 (10 mg/kg) with respect to time (days); and (C) a bar graph of tumor weight (mg) in male nude mice injected with 22Rv1 cells injected with a vehicle and/or PCNA-I1 (10 mg/kg) with respect to treatment;

FIG. 21 depicts the therapeutic effects of PCNA-I1 in animal tumor models, including: (A) a graph of body weight (g) of male nude mice implanted with LNCaP cells injected with a vehicle, PCNA-I1 (10 mg/kg) or PCNA-I1 (50 mg/kg) with respect to time (days); and (B) a bar graph of serum biochemistry of male nude mice implanted with LNCaP cells of SGPT (IU/L), SGOT (IU/L), and BUN (mg/dL) with respect to treatment with PCNA-I1; and FIG. 22 is an immunohistochemistry staining of H&E and PCNA of a LNCaP tumor in a control and in mice treated with PCNA-I1 (10 mg/kg three times/week).

Skilled artisans appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments of the present invention.

The following terms are used in the present application:

As used herein, in the context of cell growth, the terms "inhibit", "inhibits", and "inhibiting" describe preventing, reducing, and/or terminating cell replication and division. For example, cell growth is inhibited wherein cell replication is reduced compared to normal cell replication. For normal cells, normal cell growth is characterized by immortalized mouse lung and prostate endothelial cells (MuLu-Endo and MuPr-Endo), primary human umbilical endothelial cells (HUVEC), primary bone marrow mesenchymal stem cells (HuMSC), primary human mammary epithelial cells (HuBrEC), primary human prostate epithelial cells (HuPrEC), and primary mouse spleen lymphocytes and bone marrow stromal cells. For tumor cells, normal cell growth is characterized by PC-3, LNCaP, and DU-145 human prostate cancer cells. In one embodiment, inhibition of cell growth was calculated using the following formula: Growth Inhibition (%)=$(1-A_{570}$ of treated/$A_{570}$ of control)$\times 100$.

As used herein, in the context of cell growth, the term "growth" describes cell replication and division. Accordingly, as used herein, the term "growth" encompasses cell proliferation wherein cells grow or multiply by rapidly producing new cells.

As used herein, the term "effective amount" describes the amount necessary or sufficient to realize a desired biologic effect. The effective amount for any particular application may vary depending on a variety of factors, including but not limited to the particular composition being administered, the size of the subject or sample, and/or the severity of the disease and/or condition being treated.

As used herein, the term "desired biologic effect" describes inhibiting growth of a cell; modulating the function of PCNA; and decreasing, reducing, eradicating, inhibiting, and/or otherwise terminating the growth of a cancer cell or tumor. For example, desired biologic effects include, but should not be limited to, inhibiting growth of a cell by up to about 100%, inducing apoptosis of a cell, decreasing association of PCNA with chromatin, enhancing trimer formation of PCNA, and reducing growth of a tumor of prostate cancer cells. In one specific embodiment, desired biologic effects include reducing growth of a tumor of human prostate cancer cells.

As used herein, the term "tumor cell" describes a cell which exhibits uncontrolled cell division and the ability to metastasize, or to establish new growth in additional sites.

As used herein, the term "normal cell" describes a cell which does not exhibit uncontrolled cell growth and the ability to metastasize.

Following long-standing patent law convention, the terms "a," "an," and "the" refer to "one or more" when used in this application, including the claims. Thus, for example, reference to "a cell" includes a plurality of such cells, and so forth.

As used herein, in the context of PCNA, the terms "modulate", "modulates", and "modulating" describe preventing, reducing, enhancing and/or terminating the function of PCNA in cellular processes and/or describe stabilizing the PCNA trimer. For example, modulating PCNA function includes, but should not be limited to preventing, reducing, enhancing, and/or terminating PCNA function in DNA replication, DNA repair, chromatin remodeling, sister-chromatid cohesion, cell-cycle control and regulation, and/or chromatin assembly and maintenance in eukaryotic cells.

As used herein, in the context of PCNA trimer formation, the terms "enhance", "enhances", and "enhancing" describe an increased level of PCNA trimer as compared to a normal level of PCNA trimer. For example, in SDS-PAGE analysis, a normal level of PCNA trimer is from less than about 1% to about 5%, or alternatively from about 1% to about 2%, or alternatively about 5% of total PCNA (including both free form PCNA and trimer PCNA).

As used herein, in the context of a PCNA trimer, the terms "stabilize", "stabilizes", and "stabilization" describe reducing the kinetics of disassociation of the PCNA trimer.

As used herein, in the context of PCNA, the terms "associate" and "association" describe the interaction of PCNA with proteins, nucleic acids, and/or combinations thereof for which PCNA has a binding affinity. For example, in the context of PCNA association with chromatin, PCNA association with chromatin is reduced wherein PCNA association with chromatin is less than a normal level. For normal cells, a normal level of PCNA associated with chromatin is characterized by immortalized mouse lung and prostate endothelial cells (MuLu-Endo and MuPr-Endo), primary human umbilical endothelial cells (HUVEC), primary bone marrow mesenchymal stem cells (HuMSC), primary human mammary epithelial cells (HuBrEC), primary human prostate epithelial cells (HuPrEC), and primary mouse spleen lymphocytes and bone marrow stromal cells. For tumor cells, a normal level of PCNA associated with chromatin is characterized by PC-3, LNCaP, and DU-145 human prostate cancer cells. Additionally, the terms "interact", "interaction", "bind", and "binding" are used interchangeably.

As used herein, in the context of a tumor eradication, the terms "eradicate" and "eradication" describe a situation wherein a tumor is macroscopically undetectable.

As used herein, the term "carbonyl" describes the group

As used herein, the term "independently selected from," describes that the referenced groups can be identical, different, or a mixture including some identical groups and some different groups, unless the context clearly indicates otherwise. For example, the phrase "B and E are independently selected from the group consisting of —$CR_4$ and —$NR_4$" would include the scenario wherein B and E are the same, or wherein B and E are different, and any mixtures thereof.

As used herein, the terms "halo," "halide," or "halogen" describe fluoro, chloro, bromo, and iodo groups.

As used herein, the term "hydroxyl" describes the —OH group.

As used herein, the term "nitro" describes the —$NO_2$ group.

As used herein, the term "cyano" describes the —C≡N group.

As used herein, the term "alkyl" describes a $C_{1-4}$ saturated monovalent hydrocarbon radical which can be linear (i.e., "straight-chain") such as methyl, ethyl, propyl, and butyl, or branched such as isopropyl, isobutyl, and tert-butyl groups.

Throughout the specification and claims, a given chemical formula or name shall encompass all tautomers and optical and stereoisomers, as well as racemic mixtures where such isomers and mixtures exist.

Embodiments of the present disclosure relate to methods for inhibiting growth of a cell, modulating function of proliferating cell nuclear antigen in a cell, treating prostate cancer, and enhancing trimer formation of proliferating cell nuclear antigen.

I. Method for Inhibiting Growth of a Cell

In one embodiment, a method for inhibiting growth of a cell is disclosed. The method comprises contacting the cell with an effective amount of a compound, wherein the compound is selected from the group consisting of:

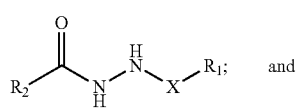

Formula (I)

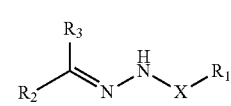

Formula (II)

wherein:

X is selected from the group consisting of carbonyl and

$R_1$ is selected from the group consisting of

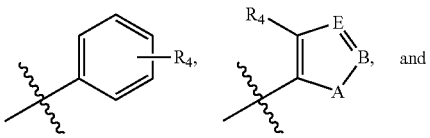

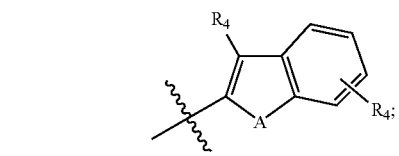

A is selected from the group consisting of —$NR_4$ and S;

B and E are independently selected from the group consisting of —$CR_4$ and —$NR_4$;

each $R_4$ is independently selected from the group consisting of H, halo, nitro, cyano, hydroxyl, carbonyl, a $C_1$-$C_4$ alkyl, —$OR_3$, and —$N(R_3)_2$;

$R_3$ is selected from the group consisting of H and a $C_1$-$C_4$ alkyl; and $R_2$ is selected from the group consisting of

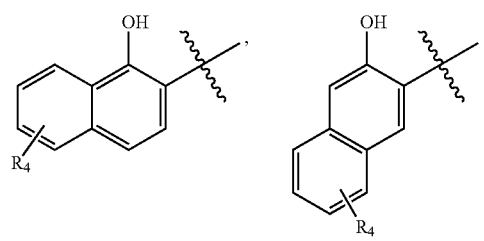

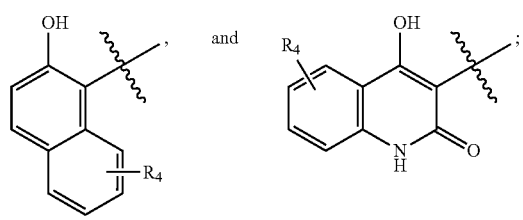

and tautomers thereof.

As drawn, every position on the rings of the $R_1$ and $R_2$ groups has an $R_4$ group. The compounds of Formula I and Formula II, including tautomeric, enantiomeric or diastereomeric forms and pharmaceutically acceptable salts, prodrugs, or metabolites thereof, are all referred to herein as "PCNA-I" or "PCNA-I's." Examples of PCNA-I's are shown in Table I, below. Additionally, the compounds shown in Table I will be referred to herein as their "Compound Number", i.e. PCNA-I1-PCNA-I11.

TABLE I
Exemplary Compounds
| Compound Number | Structure |
|---|---|
| PCNA-I1 | 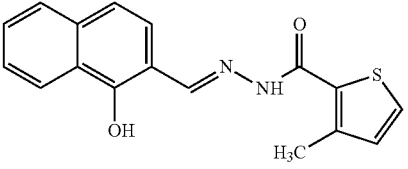 [SMILES: Cc1ccsc1C(=O)N/N=C/c1ccc2ccccc2c1O] |
| PCNA-I2 | 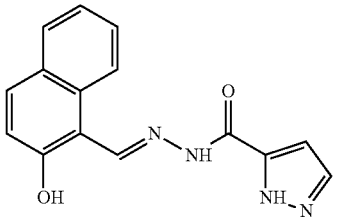 [SMILES: O=C(N/N=C/c1c(O)ccc2ccccc12)c1ccn[nH]1] |
| PCNA-I3 | 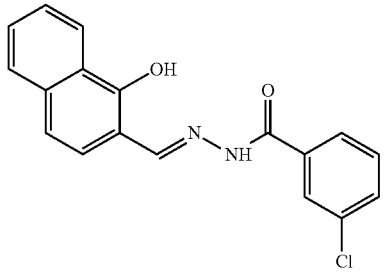 [SMILES: O=C(N/N=C/c1ccc2ccccc2c1O)c1cccc(Cl)c1] |
| PCNA-I4 | 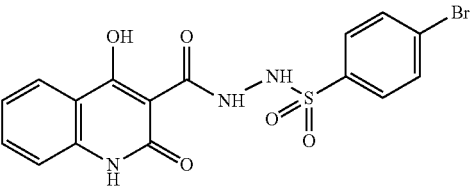 [SMILES: O=C(NNS(=O)(=O)c1ccc(Br)cc1)c1c(O)c2ccccc2[nH]c1=O] |
| PCNA-I5 | 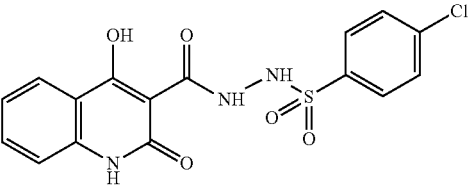 [SMILES: O=C(NNS(=O)(=O)c1ccc(Cl)cc1)c1c(O)c2ccccc2[nH]c1=O] |
| PCNA-I6 | 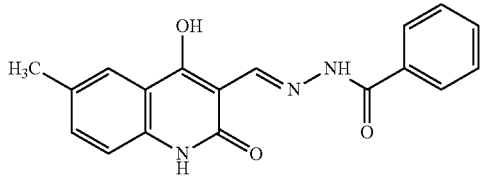 [SMILES: Cc1ccc2[nH]c(=O)c(/C=N/NC(=O)c3ccccc3)c(O)c2c1] |

TABLE I-continued

Exemplary Compounds

| Compound Number | Structure |
|---|---|
| PCNA-I7 | 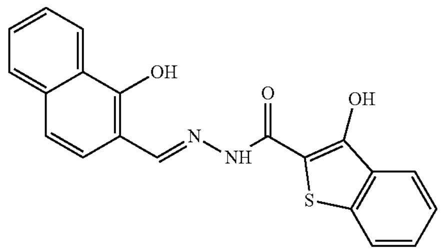 [SMILES: O=C(N/N=C/c1ccc2ccccc2c1O)c1sc2ccccc2c1O] |
| PCNA-I8 | 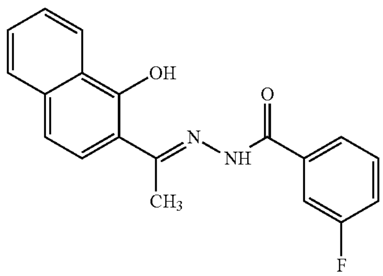 [SMILES: C/C(=N\NC(=O)c1cccc(F)c1)c1ccc2ccccc2c1O] |
| PCNA-I9 | 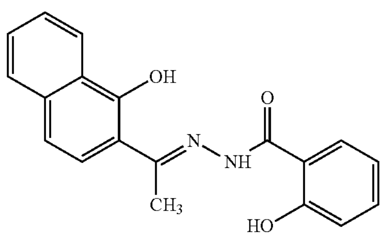 [SMILES: C/C(=N\NC(=O)c1ccccc1O)c1ccc2ccccc2c1O] |
| PCNA-I10 | 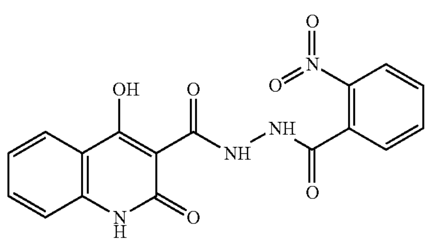 [SMILES: O=C(NNC(=O)c1c(O)c2ccccc2[nH]c1=O)c1ccccc1[N+](=O)[O-]] |
| PCNA-I11 | |

In this embodiment, the growth of the cell is inhibited by from about 5 to about 100% or alternatively from about 20% to about 80% or from about 30% to about 50%, or alternatively about 50%. Wherein cell growth is inhibited by about 50%, the PCNA-I is provided in a concentration of from about 0.03 µM to about 40 µM, or alternatively from about 0.1 µM to about 10 µM, or alternatively from about 1 µM to about 3 µM, or about 10 µM. More particularly, wherein cell growth of a normal cell is inhibited by about 50% (hereinafter "IC$_{50}$"), the PCNA-I's are provided at an average concentration of from about 0.1 µM to about 10 µM, with IC$_{50}$ values of about 1.43±0.45 µM. Additionally, wherein cell growth of a tumor cell is inhibited by about 50% (IC$_{50}$), the PCNA-I's are provided at an average concentration of from about 0.03 µM to about 10 µM, or alternatively from about 0.1 µM to about 10 µM, or alternatively from about 1 µM to about 2 µM, with IC$_{50}$ values of about 0.19±0.09 µM.

In another embodiment, contacting the cells with a single amount of PCNA-I's inhibited cell growth for up to about seven days.

In one particular embodiment, the growth of the cell is inhibited independent of growth rate of the cell. Accordingly, the growth of the cell is inhibited regardless of whether the cell is a normal cell or a tumor cell. Accordingly, in one embodiment, tumor cells were more susceptible to PCNA-I's than normal cells. For example, tumor cells were from about three to about twenty times, or alternatively from about five to about ten times, or alternatively about three times more susceptible to PCNA-I's than normal cells.

In another embodiment, the growth of the cell was inhibited such that cell death, i.e. apoptosis, was induced. In one embodiment, PCNA-I's provided at a concentration of from about 1 to about 10 µM, or from about 2 to about 8 µM, or from about 3 to about 5 µM, induced apoptosis in tumor cells.

In one particular embodiment, a combination therapy for inhibiting cell growth is disclosed. Specifically, the combination therapy for inhibiting cell growth includes contacting the cell with an effective amount of cisplatin in addition to the PCNA-I's. The cisplatin may be administered (or come into contact with the cell) to the cell substantially simultaneously, contemporaneously, or staggered from the administration of (or the cell's contact with) the PCNA-I's. Administration of cisplatin may be contemporaneous in that the administration of cisplatin overlaps with the administration of the PCNA-I's, but is not necessarily simultaneous. Administration of cisplatin may be staggered with the administration of the PCNA-I's such that it is administered before or after the administration of the PCNA-I's, but is not necessarily simultaneous or contemporaneous.

The combination therapy of cisplatin with the PCNA-I's may reduce the amount of cisplatin administered. For example, additive or synergistic effects were observed when a tumor cell is treated with a combination of cisplatin and PCNA-I1. In one particular embodiment, the combination therapy of cisplatin and PCNA-I's is synergistic with regard to cell growth inhibition wherein cisplatin is contacted with the cell at a concentration of from about 0.1 to about 10 µM, or alternatively from about 0.5 to about 5 µM, or from about 0.3 to about 1 µM. Other DNA damage drugs which may be useful in inhibiting cell growth in combination with the PCNA-I's include, but should not be limited to, Bleomycin, alkylators, nitrosourears, mitomycin C, anthracyllines, aminoacridines, ellipticines, epipodophyllotoxins, and camptothecin. A combination of PCNA inhibitory compounds with these chemotherapeutic drugs may also produce the synergistic effects as we observed in a cell treated with PCNA-I1 and cisplatin.

Moreover, the combination therapy of cisplatin and the PCNA-I's induced synergistic effects in terms of Poly ADP Ribose Polymerase (hereinafter "PARP") cleavage, p53 phosphorylation, and expression of p21. In one particular embodiment, the combination therapy of cisplatin and PCNA-I's is synergistic with regard to PARP cleavage, p53 phosphorylation, and expression of p21 wherein cisplatin is contacted with the cell at a concentration of from about 0.1 to about 10 µM, or from about 0.5 to about 5 µM, or from about 0.3 to about 1 µM. When the administration of cisplatin is staggered with the administration of the PCNA-I's, cisplatin is administered within about ½ H to about 8 H, or alternatively about 1H to about 4 H, or about 4 H of the administration of the PCNA-I's.

In one specific embodiment, the combination therapy for inhibiting cell growth includes contacting the cell with cisplatin and the compound of Formula (I). Examples of PCNA-I's of Formula (I) which may be employed to inhibit cell growth include PCNA-I4, PCNA-I5, and PCNA-I10. In another embodiment, the combination therapy for inhibiting cell growth includes contacting the cell with cisplatin and the compound of Formula (II). Examples of PCNA-I's of Formula (II) which may be employed to inhibit cell growth include PCNA-I1, PCNA-I2, PCNA-I3, PCNA-I6, PCNA-I7, PCNA-I8, PCNA-I9, and PCNA-I11. In one specific embodiment, the compound employed to inhibit cell growth is at least one of PCNA-I1 and PCNA-I2.

In another embodiment, the cells employed in the methods disclosed herein include mammalian cells. More specifically, the cells may be human cells, non-human primate cells, canine cells, feline cells, murine cells, bovine cells, equine cells, porcine cells, and lagomorph cells. Additionally, the cells employed in the methods disclosed herein include tumor cells and normal cells. Examples of tumor cells include, but should not be limited to, breast cancer cells, prostate cancer cells, colon cancer cells, cervical cancer cells, melanoma cells, colon cancer cells, multidrug resistant colon cancer cells, and fibrosarcoma cells. More specifically, specific tumor cell lines which may be employed in the methods disclosed herein include, but should not be limited to, MCF-7, T47D, PC-3, DU145, 22Rv1, LAPC-4, LNCaP, A375, MDA-MB435, TRAMP-C2RE3, B16, K1735, and UV2237. With regard to LNCaP and 22Rv1 cells, both express prostatic specific antigen (hereinafter "PSA"). LNCaP cells express wildtype p53 tumor suppressor gene and 22Rv1 cells express mutant p53 tumor suppressor gene.

Examples of normal cells include, but should not be limited to, blood vessel endothelial cell cells, bone marrow mesenchymal stem cells, mammary epithelial cells, prostate epithelial cells, spleen lymphocytes, lung endothelial cells, and prostate endothelial cells. More specifically, specific normal cell lines which may be employed in the methods disclosed herein include, but should not be limited to, HUVEC, mesenchymal stem cell epithelia cells, epithelial cells, lung endothelial cells (immortal), prostate endothelia cells, stroma cells, and lymphocytes.

In one particular embodiment, the compound employed to inhibit cell growth is the compound of Formula (I). Examples of PCNA-I's of Formula (I) which may be employed to inhibit cell growth include PCNA-I4, PCNA-I5, and PCNA-I10. In another embodiment, the compound employed to inhibit cell growth is the compound of Formula (II). Examples of PCNA-I's of Formula (II) which may be employed to inhibit cell growth include PCNA-I1, PCNA-I2, PCNA-I3, PCNA-I6, PCNA-I7, PCNA-I8, and PCNA-I9. In one specific embodiment, the compound employed to inhibit cell growth is at least one of PCNA-I1 and PCNA-I2.

PCNA-I's may also be employed to inhibit cell cycle distribution. Specifically, PCNA-I's may be employed to moderate cell accumulation in the G1 phase of the cell cycle and an S and G2/M phase arrest of the cell cycle. In particular, cells contacted with PCNA-I's at a concentration of from about three to about five times the concentration of PCNA-I's required to inhibit cell growth by about 50% resulted in S and G2/M phase arrest of the cell cycle.

II. Method for Modulating Function of PCNA

In another embodiment, a method for modulating function of PCNA in a cell is disclosed. The method includes contacting the cell with an effective amount of a compound, wherein the compound is selected from the group consisting of:

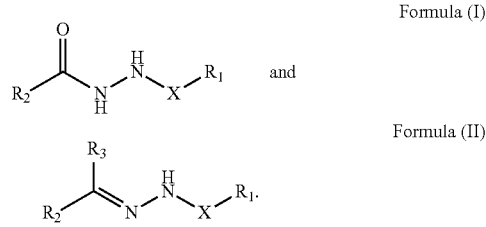

In one embodiment, the function of the PCNA is modulated by reducing association of the PCNA with chromatin. Specifically, the function of the PCNA is modulated by reducing association of the PCNA with euchromatin and/or heterochromatin.

In another embodiment, the function of the PCNA is modulated by enhancing trimer formation of the PCNA. In one embodiment, the trimer formation of PCNA was increased from about 5 to about 10 times, or alternatively from about 6 to about 8 times, or alternatively from about 7 times, that of a normal level of PCNA in normal cells. In another embodiment, the function of the PCNA is modulated by stabilizing the PCNA.

In one particular embodiment, the compound employed to modulate PCNA function is the compound of Formula (I). Examples of PCNA-I's of Formula (I) which may be employed to modulate PCNA function include PCNA-I4, PCNA-I5, and PCNA-I10. In an alternative embodiment, the compound employed to modulate PCNA function is the compound of Formula (II). Examples of PCNA-I's of Formula (II) which may be employed to modulate PCNA function include PCNA-I1, PCNA-I2, PCNA-I3, PCNA-I6, PCNA-I7, PCNA-I8, PCNA-I9, and PCNA-I11. In one specific embodiment, the compound employed to modulate PCNA function is at least one of PCNA-I1 and PCNA-I2.

III. Method for Treating Prostate Cancer

In yet another embodiment, a method for treating prostate cancer in a subject in need thereof disclosed. The method includes administering an effective amount of a compound to the subject, wherein the compound is selected from the group consisting of:

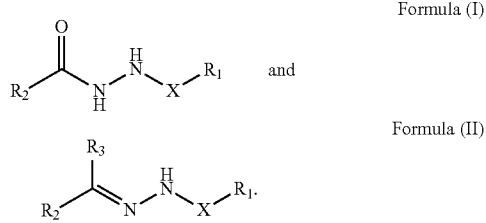

In one embodiment, growth of the prostate tumor is reduced. More specifically, volume of the prostate tumor is reduced by from about 50% to about 90%, or alternatively from about 70% to about 90%, or alternatively from about 70% to about 85%, or alternatively about 70%. In another embodiment, tumor volume is reduced by from about 300 to about 5000 mm$^3$, or alternatively from about 1000 to about 3000 mm$^3$, or alternatively about 3500 mm$^3$. In one specific embodiment, the prostate tumor is eradicated. The prostate tumor may be eradicated following administration of PCNA-I's for from about six to about seven weeks. In one specific embodiment, the prostate tumor may be eradicated following administration of PCNA-I's for about seven weeks.

In one embodiment, the PCNA-I's are administered systemically. Systemic administration of the PCNA-I's include oral, subcutaneous, intravenous, intramuscular, and intraperitoneal administration. In one embodiment, the PCNA-I's are administered in a dose of from about 10 to about 50 µg/g, or alternatively from about 20 to about 30 µg/g, or about 10 µg/g. The dose of the PCNA-I's are administered every other day. More specifically, the dose of the PCNA-I's are administered about three times per week.

In one embodiment, the subject is a mammal. The mammal may be a human, a non-human primate, a canine, a feline, a murine, a bovine, an equine, a porcine, and a lagomorph. In one particular embodiment, the mammal is a human.

In one particular embodiment, the compound employed to treat prostate cancer is the compound of Formula (I). Examples of PCNA-I's of Formula (I) which may be employed to treat prostate cancer include PCNA-I4, PCNA-I5, and PCNA-I10. In another embodiment, the compound employed to treat prostate cancer is the compound of Formula (II). Examples of PCNA-I's of Formula (II) which may be employed to treat prostate cancer include PCNA-I1, PCNA-I2, PCNA-I3, PCNA-I6, PCNA-I7, PCNA-I8, PCNA-I9, and PCNA-I11. In one specific embodiment, the compound employed to treat prostate cancer is at least one of PCNA-I1 and PCNA-I2.

The compound employed to treat prostate cancer may be employed to treat the following non-limiting types of prostate cancer: androgen-dependent and androgen independent prostate cancer.

In another embodiment, a pharmaceutical composition is disclosed. In one particular embodiment, the pharmaceutical composition comprises Formula (I) or Formula (II). In another embodiment, the compound is formulated for administration to a subject for the treatment of prostate cancer. In this particular embodiment, a method for treating prostate cancer in a subject in need thereof is also provided, wherein the method comprises administering an effective amount of the pharmaceutical composition to the subject.

In one particular embodiment, the pharmaceutical composition may further comprise a pharmaceutically acceptable carrier. Pharmaceutically acceptable carriers include a wide range of known diluents (i.e., solvents), fillers, extending agents, binders, suspending agents, disintegrates, surfactants, lubricants, excipients, wetting agents and the like commonly used in this field. These carriers may be used singly or in combination according to the form of the pharmaceutical preparation. The resulting preparation may incorporate, if necessary, one or more solubilizing agent, buffers, preservatives, colorants, perfumes, flavorings and the like that are widely used in the field of pharmaceutical preparation.

The compound of Formula (I) or Formula (II) may be formulated into a dosage form selected from the group consisting of tablets, capsules, granules, pills, injections, solutions, emulsions, suspensions, and syrups. The form and administration route for the pharmaceutical composition are not limited and can be suitably selected. For example, tablets, capsules, granules, pills, syrups, solutions, emulsions, and suspensions may be administered orally. Additionally, injections (e.g. subcutaneous, intravenous, intramuscular, and intraperitoneal) may be administered intravenously either singly or in combination with a conventional replenisher containing glucose, amino acid and/or the like, or may be singly administered intramuscularly, intracutaneously, subcutaneously and/or intraperitoneally.

The pharmaceutical composition of the invention for treating prostate cancer may be prepared according to a method known in the pharmaceutical field of this kind using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

Injections, solutions, emulsions, suspensions, syrups and the like may be prepared according to a known method suitably using solvents for dissolving the active ingredient, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

The proportion of the active ingredient to be contained in the pharmaceutical composition of the invention for treating prostate cancer can be suitably selected from a wide range.

IV. Method for Enhancing PCNA Trimer Formation

In still yet another embodiment, a method for enhancing trimer formation of PCNA is disclosed. The method includes contacting the PCNA with an effective amount of a compound, wherein the compound is selected from the group consisting of:

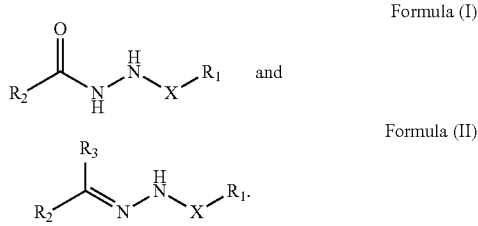

In one embodiment, the PCNA may be selected from the group consisting of recombinant PCNA and PCNA in a cell, as previously discussed in an earlier section. Accordingly, the PCNA-I's may be employed as a research tool to enhance trimer formation. Trimer formation is enhanced as previously discussed in an earlier section.

Additionally, a method for stabilizing a PCNA trimer is disclosed. The method includes contacting the PCNA with an effective amount of a compound, wherein the compound is Formula (I) or Formula (II).

EXAMPLES

The following non-limiting examples illustrate the methods of the present disclosure. Data shown in the examples are the mean±standard deviation. Differences between means were compared using the two-tailed Student's t test and were considered significantly different at the level of $p<0.05$.

Example 1: Effects of PCNA-I1 and PCNA-I2 on Cell Growth

Experimental Protocol.

Growth inhibitory effects of PCNA-I1 and PCNA-I2 were assessed in human cancer cell lines, mouse cancer cell lines, immortalized mouse cell lines, and human primary cell lines. Specifically, growth inhibitory effects of PCNA-I1 and PCNA-I2 were assessed using MTT staining in the following cells lines: 1) human cancer cell lines including LNCaP (androgen receptor negative), 22Rv1, DU-145, LAPC-4, and PC-3 (androgen receptor positive) prostate cancer cells; MCF-7 and T47D breast cancer cells; A375 and MDA-MB435 melanoma cells; 2) mouse cancer cell lines including TRAMP-C2RE3 prostate cancer cells, B16 and K1735 melanoma cells, UV2237 fibrosarcoma cells, and CT-26 colon cancer cells; 3) immortalized mouse lung cell lines and mouse endothelial cell lines; and 4) primary human cell lines including umbilical endothelial cells (HUVEC, PromoCell, Heidelberg, Germany), primary bone marrow mesenchymal stem cells (HuMSC, PromoCell), primary human mammary epithelial cells (HuBrEC, Lonza, Walkersville, Md.), primary human prostate epithelial cells (HuPrEC, Lonza), and primary mouse spleen lymphocytes (isolated in this laboratory), and primary mouse bone marrow stromal cells (isolated in this laboratory). PCNA-I1 and PCNA-I2 were either provided by the University of Cincinnati Drug Discovery Center (UC-DDC, Cincinnati, Ohio) or were purchased from Chembridge Co (San Diego, Calif.), ChemDiv (San Diego, Calif.), and/or Sigma-Aldrich (St Louis, Mo.).

Growth inhibitory effects of the compounds were assessed by MTT staining as described previously by Dong et al. in *In Vitro Model for Intrinsic Drug Resistance: Effects of Protein Kinase C Activators on the Chemosensitivity of Cultured Human Colon Cancer Cells*; Mol. Pharmacol. 1991; 39: 563-9. Briefly, cells were cultured and treated in their respective media. Cells were plated into 96-well plates at 1000 to 5000 cells/well. After an overnight incubation, the cells were treated for four days with various concentrations (up to 10 µM) of PCNA-I1 or PCNA-I2. The live cells were stained with MTT and cells in exponential growth phase were harvested by a one to three minute treatment with a 0.25% trypsin-0.02% EDTA solution. Flasks were tapped to detach the cells, RPMI 1640-10% FBS was added, and the cell suspensions were gently agitated to produce single-cell suspensions. The cell suspensions were washed and resuspended in medium with supplements specified for different cells. Only suspensions of single cells with a viability exceeding 95% (ascertained by trypan blue exclusion) were used.

$IC_{50}$ values were derived from growth inhibition curves. Data for tumor cells are a mean of five to seven experiments. Data for primary cells are a mean of three experiments. The means of $IC_{50}$ for tumor cells and normal cells were about 0.19±0.09 and 1.43±0.45, respectively (p=0.0001). Inhibition of cell growth was calculated using the formula: growth inhibition (%)=(1−$A_{570}$ of treated/$A_{570}$ of control)×100. $IC_{50}$ (the concentration that inhibited cell growth by 50%) values were also determined. For evaluation of lymphocyte growth in suspension, an Alamar blue assay was performed, wherein freshly prepared mouse spleen lymphocytes were stimulated for 72 H with 2 ug/mL concanavalin A (Sigma Chemicals, St. Louis, Mich.). During the last 24 H, 20 µl/well of Alamar blue (Invitrogen, Carlsbad, Calif.) was added. The fluorescence intensity was measured at 530/580 (excitation/emission) in the FLUOstar Omega microplate reader (BMG LABTECH, Cary, N.C.).

The necessity of a continuous presence of PCNA-I1 for cell growth was also investigated. Specifically, PC-3 cells were treated with 0.5 µM PCNA-I1 for 24 H. After washing, the PC-3 cells were seeded into a 96-well plate (1000 cells/well) and stained with Alamar blue, which revealed the presence of healthy cells and was suitable for assessing cell growth in both adherent and suspension cultures, at an interval of 24 H for up to 144 H.

Experimental Results.

As shown in Table II below, PCNA-I1 and PCNA-I2 had $IC_{50}$ values in the nM (PCNA-I1) or nM to low µM (PCNA-I2) range in the following prostate cancer cell lines: PC-3, DU145, and LNCaP.

TABLE II

IC$_{50}$ Values of PCNA-I1 and PCNA-I2 (µM)

| Species | Tissue Origin | Cell Line | PCNA-I1 | PCNA-I2 |
|---|---|---|---|---|
| Tumor Cells | | | | |
| Human | Breast | MCF-7 | 0.15 | 1.01 |
| | | T47D | 0.15 | N.D. |
| | | PC-3 | 0.24 | 0.97 |
| | | DU145 | 0.16 | 1.19 |
| | | 22Rv1 | 0.18 | N.D. |
| | | LAPC-4 | 0.30 | 1.79 |
| | | LNCaP | 0.14 | 0.56 |
| | Melanoma | A375 | 0.29 | 3.75 |
| | | MDA-MB435 | 0.29 | N.D. |
| Mouse | Prostate | TRAMP-C2RE3 | 0.20 | N.D. |
| | Melanoma | B16 | 0.35 | N.D. |
| | | K1735 | 0.05 | N.D. |
| | Fibrosarcoma | UV2237 | 0.25 | N.D. |
| | | | 0.13 | N.D. |
| | | | 0.08 | N.D. |
| | | | 0.07 | N.D. |
| | Mean ± SD | | 0.19 ± 0.09 | N.D. |
| Normal Cells | | | | |
| Human | Blood Vessel | HUVEC | 1.54 | N.D. |
| | Bone Marrow | Mesenchymal Stem Cells | 0.99 | N.D. |
| | Breast | Epithelial Cells | 1.67 | N.D. |
| | Prostate | Epithelial Cells | 2.00 | N.D. |
| Mouse | Blood Vessel | Lung Endothelial Cells (immortal) | 1.16 | N.D. |
| | | Prostate Endothelial | 0.68 | N.D. |
| | Bone Marrow | Stroma Cells | 1.90 | N.D. |
| | Spleen | Lymphocytes | 1.50 | N.D. |
| | Mean ± SD | | 1.43 ± 0.45 | N.D. |

Referring to Table II, PCNA-I1 inhibited growth of all tumor cells, regardless of tissue origin, with IC$_{50}$ values in the nM range. Additionally, the CT26R100 and CT26-R500 murine colon cancer cell lines (which overexpress P-glycoprotein and exhibit a multidrug resistance (MDR) phenotype) were even more sensitive to PCNA-I1 than the parental CT26 cells. Additionally, PCNA-I2 was about three to five times less potent than PCNA-I1 in most cell lines examined. PCNA-I1 also inhibited the growth of primary cultures of bone marrow mesenchymal stem cells, endothelial cells, lymphocytes, mammary epithelial cells, and prostate epithelial cells, as well as the immortalized mouse lung and prostate endothelial cells. However, the potency of PCNA-I1 on growth of all primary and immortalized normal cells was significantly lower than that of tumor cells. The concentrations of PCNA-I1 that inhibited growth of normal cells by 50% were approximately 8 times higher than those for tumor cells (p<0.001).

CT-26R100 and CT-26R500 cells were derived from CT-26 murine colon cancer cells by long-term culture of the cells in the presence of increasing concentrations of doxorubicin. CT-26R100 and CT-26R500 cells express high levels of multidrug resistant gene and are ten to fifty times more resistant than their parental cells to doxorubicin, taxol, and many other chemotherapeutic drugs. CT-26R100 and CT-26R500 cells were as susceptible as the parental CT-26 cells to the inhibitory effects of PCNA-I1.

Figure 1:
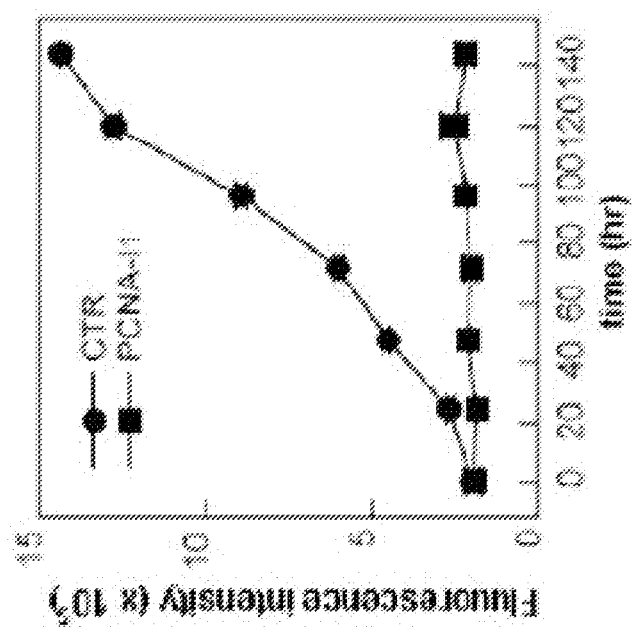

Additionally, as shown in FIG. 1, a single one-day pretreatment with PCNA-I1 in PC-3 cells was sufficient to inhibit cell growth for up to seven days. Specifically, the fluorescence intensity in culture of control cells revealed that the viable cell densities and/or numbers, increased in a time-dependent manner. In contrast, the fluorescence intensity in wells containing cells exposed to PCNA-I1 never significantly changed during the entire incubation period.

Example 2: Effects of PCNA-I3, PCNA-I4, PCNA-I6, PCNA-I7, PCNA-I8, PCNA-I9, and PCNA-I10 on Cell Growth Experimental Protocol.

Growth inhibitory effects of PCNA-I3, PCNA-I4, PCNA-I6, PCNA-I7, PCNA-I8, PCNA-I9 and PCNA-I10 were assessed in human prostate cancer cell lines. Specifically, growth inhibitory effects of PCNA-I3, PCNA-I4, PCNA-I6, PCNA-I7, PCNA-I8, PCNA-I9 and PCNA-I10 were assessed using MTT staining in LNCaP and PC-3 cells. PCNA-I3, PCNA-I4, PCNA-I6, PCNA-I7, PCNA-I8, PCNA-I9 and PCNA-I10 were either provided by the University of Cincinnati Drug Discovery Center (UC-DDC, Cincinnati, Ohio) or were purchased from Chembridge Co (San Diego, Calif.), ChemDiv (San Diego, Calif.), and/or Sigma-Aldrich (St Louis, Mo.).

Growth inhibitory effects of the compounds were assessed by MTT staining as described previously by Dong et al. as discussed above. Briefly, cells were cultured and treated in their respective media. Cells were plated into 96-well plates at 1000 to 5000 cells/well. After an overnight incubation, the cells were treated for four days at various concentrations (up to 10 µM) of PCNA-I1 or PCNA-I2. The live cells were stained with MTT and cells in exponential growth phase were harvested by a one to three minute treatment with a 0.25% trypsin-0.02% EDTA solution. Flasks were tapped to detach the cells, RPMI 1640-10% FBS was added, and the cell suspensions were gently agitated to produce single-cell suspensions. The suspensions were washed and resuspended in medium with supplements specified for different cells. Only suspensions of single cells with viability exceeding 95% (ascertained by trypan blue exclusion) were used.

IC$_{50}$ values were derived from growth inhibition curves. Data shown for tumor cells are a mean of two experiments. Inhibition of cell growth was calculated using the formula: growth inhibition (%)=(1−A$_{570}$ of treated cells/A$_{570}$ of control cells)×100. IC$_{50}$ (the concentration that inhibited cell growth by 50%) values were also determined.

Experimental Results.

As shown in Table III below, PCNA-I3, PCNA-I4, PCNA-I6, PCNA-I7, PCNA-I8, PCNA-I9 and PCNA-I10 also inhibited the growth of PC-3 and LNCaP cells. The effects of PCNA-I5 were not determined in these experiments, as PCNA-I5 has a structure which is almost identical to PCNA-I4.

TABLE III

IC$_{50}$ Values of PCNA Inhibitors (µM)

| PCNA Inhibitor | PC-3 Cells | LNCaP Cells |
|---|---|---|
| PCNA-I3 | 0.44 | 0.26 |
| PCNA-I4 | 3.00 | 0.68 |
| PCNA-I6 | >10.0 | >10.0 |
| PCNA-I7 | 3.60 | 2.20 |
| PCNA-I8 | 1.00 | 0.68 |
| PCNA-I9 | 2.20 | 0.71 |
| PCNA-I10 | >10.0 | 2.20 |

Example 3: Differential Effects of PCNA-I1 on Tumor Cells and Primary Cells

Experimental Protocol.

The effects of PCNA-I1 on growth of tumor cells versus primary cells was also investigated. Specifically, the effects of PCNA-I1 on the growth of primary cells was investigated using primary culture of mouse lymphocytes. An Alamar blue assay was performed with PC-3 cells as a positive control. Freshly prepared mouse spleen lymphocytes were stimulated for 72 H with 2 µg/mL of concanavalin A. During the last 24 H, 20 µL/well of alamar blue was added. The fluorescence intensity was measured at 530/580 (excitation/emission).

The effects of PCNA-I1 on the growth of human bone marrow derived MSC cells (MSC, PromoCell GmbH, Heidelberg, Germany), human umbilical endothelial cells (HUVEC, PromoCell), and immortalized mouse lung (Mu-Lu-Endo), and prostate endothelial cells (Mu-Pr-Endo) were also investigated as outlined above.

Experimental Results.

Figure 2:
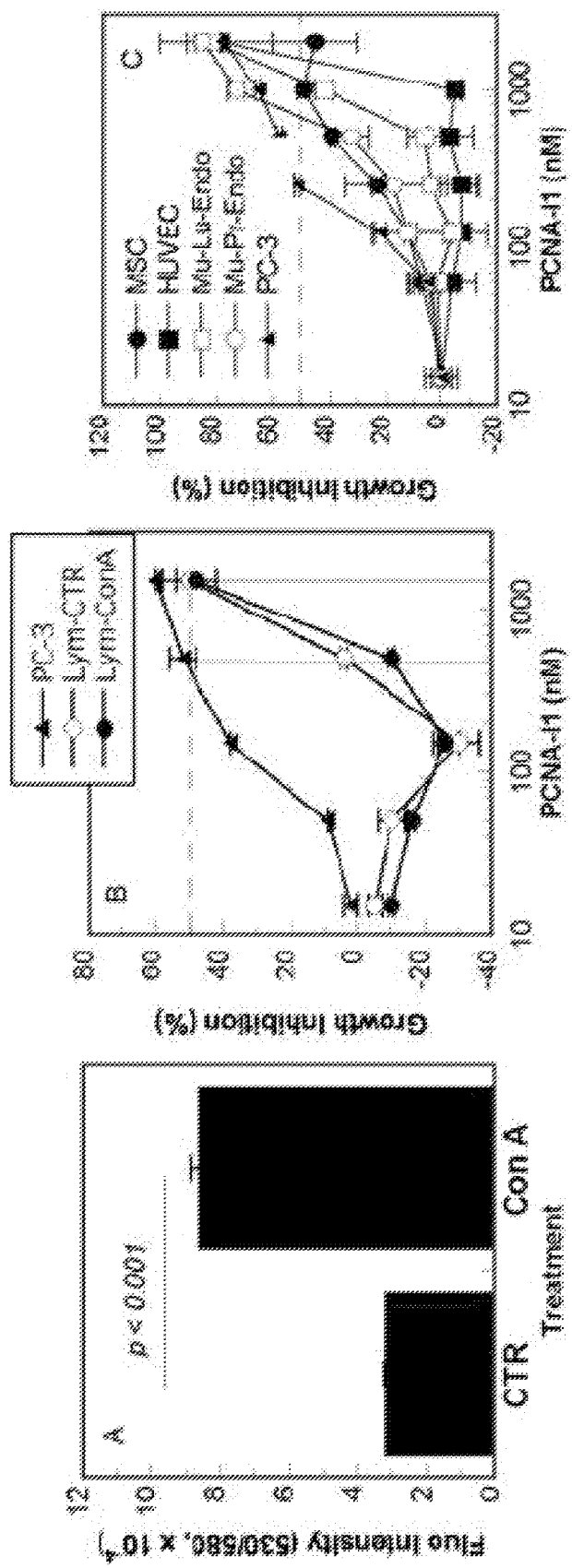

As shown in FIG. 2(A), concanavalin A stimulated growth of lymphocytes by about 3.5 fold, which was approximately equivalent to a doubling time of 24 H, a duration that is typical for most tumor cells. As shown in FIG. 2(B), PCNA-I1 inhibited growth of both lymphocytes and PC-3 cells. However, PC-3 cells were approximately three times more susceptible than lymphocytes with $IC_{50}$ values of 482 nM (PC-3) and 1500 nM (lymphocytes), respectively. PCNA-I1 promoted lymphocyte growth at concentrations below the cytotoxic or cytostatic doses, regardless of the presence or absence of concanavalin A. More interestingly, PCNA-I1 inhibited growth of both control and concanavalin A-stimulated lymphocytes to a similar extent, completely independent of cell growth rates.

As shown in FIG. 2(C), primary and immortalized cells were also less susceptible than tumor cells. The $IC_{50}$ values were 250 nM (PC-3), 989 nM (MSC), 1542 nM (HUVEC), 677 nM (Mu-Pr-Endo), and 1159 nM (Mu-Lu-Endo). Moderate growth stimulation by PCNA-I1 was noted in HUVEC and Mu-Lu-Endo cells. Accordingly, without being bound by the theory, these data suggest that the inhibitory effects of PCNA-I1 and PCNA-I2 (data not shown) were partially selective toward tumor cells.

Example 4: PCNA Expression Levels in Tumor Cells and Primary Cells

Experimental Protocol.

The expression of PCNA in tumor cells and primary cells was determined. Specifically, the expression of PCNA in the following cells lines was determined: 1) PrEC, primary prostate epithelial cells (Lonza Walkerrsville Inc., Walkerrsville, Md.); 2) LNCaP; 3) LAPC-4; 4) 22Rv1; 5) PC-3; 6) DU145 human prostate cancer cells; 7) MCF-7 human breast cancer cells; and 8) A375, human melanoma cells.

Cells were lysed in buffer A (1% Triton-100, 20 mM Tris-HCl, pH 8.0, 137 mM NaCl, 10% glycerol, 2 mM EDTA, 1 mM dithiothreitol (DTT), 1 mM phenylmethylsulfonyl fluoride (PMSF, a cocktail of protease inhibitors, Sigma). The lysate was placed on ice for 20 min and then centrifuged at 12000×g for 10 min at 4° C. The supernatant was analyzed by Western blotting.

Experimental Results.

Figure 3:
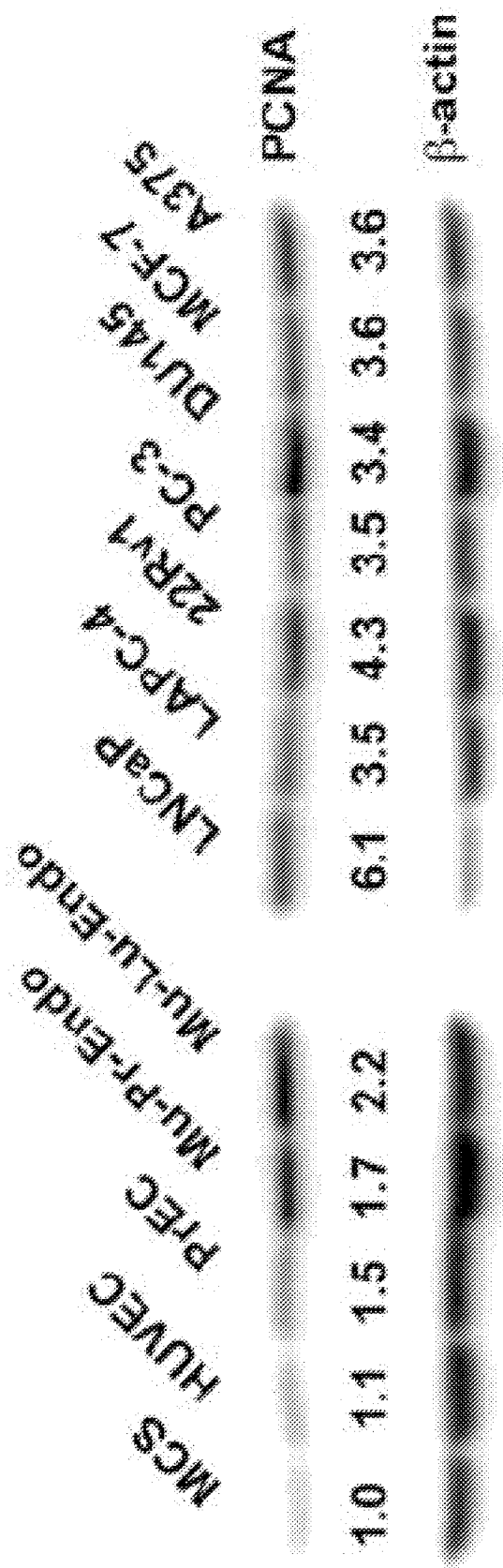
FIG. 3 is a western blot which depicts the expression of PCNA in tumor cells (LNCaP, LAPC-4, 22Rv1, PC-3, DU145, MCF-7, and A375) and in normal cells (MCS, HUVEC, PrEC, Mu-Pr-Endo, Mu-Lu-Endo)

As shown in FIG. 3, tumor cells expressed three to five fold higher levels of PCNA than primary cells. Without being bound by the theory, these data suggest that tumor cells may require a higher level of PCNA for their growth and, therefore, are more susceptible to the inhibitory effects of the inhibitors. Alternatively, without being bound by the theory, these data suggest that PCNA in tumor cells may have a higher affinity to the tested PCNA inhibitors.

Example 5: Effects of PCNA Inhibitors on Cell Cycle Distribution

Experimental Protocol.

The effects of PCNA inhibitors on cell cycle progression were investigated via flow cytometry analysis. Specifically, PC-3 cells were plated into 60 mm plates at $2\times10^5$ cells/plate and were allowed to attach overnight. After incubation in serum-free medium (SFM) for 24 H, which partially synchronized the cells in G1 phase due to serum-starvation, the cells were cultured in fresh medium or the medium supplemented with 5% FBS in the absence or presence of 1 µM PCNA-I1 (a concentration three to five times the $IC_{50}$ value for most types of tumor cells) for up to 72 H. The cells were sampled every 24 H for cell cycle distribution analysis.

The cells were rinsed with HBSS, detached by trypsinization, suspended in MEM-5% FBS, pelleted by centrifugation, resuspended in PI staining solution (PBS containing 50 µg/mL PI, 100 µg/mL RNase A, and 0.05% Triton X-100), and incubated for 45 min at 37° C. After washing with PBS, the cells were resuspended in PBS for flow cytometry analysis in an Epics-XL-MCL system (Beckman Coulter, Fullerton, Calif.). Thirty thousand cells at each time point were collected to determine their DNA content and to obtain flow cytometric fluorescence histograms (X-axis fluorescence, Y-axis cell number). The three fractions (G0/G1, G2/M and S) were quantified by using the Synchronization Wizard of ModFit LT Flow Cytometry Cell-cycle Analysis Softward (Verity Software House, Topsham, Me.).

Flow cytometry analysis was also performed on cells in which endogenous PCNA was knocked down with transfection of PCNA-specific siRNA. Specifically, PC-3 cells were plated into a 60-mm plate at $2\times10^5$/plate in antibiotics-free medium and transfected with 200 pmol PCNA specific siRNA or control scrambled siRNA for 24 H using Lifectamine 2000. The cells were then cultured in SFM for 24 H, followed by incubation in fresh SFM or stimulation with medium supplemented with 5% FBS, and sampled at different times for analyses. The PC-3 cells were also subjected to western blot analysis. Specifically, cells were washed and scraped into a lysis buffer (1% Triton X-100, 20 mM Tris-HCl, pH 8.0, 137 mM NaCl, 10% glycerol, 2 mM EDTA, 1 mM PMSF, and a protease inhibitor cocktail) and analyzed by Western blotting analysis as described by Zhang et al. in *Tumor-infiltrating Macrophages are Involved in Suppressing Growth and Metastasis of Human Prostate Cancer Cells by INF-beta Gene Therapy in Nude Mice*; Clin. Cancer Res. 2002; 8:29:2942-51. Samples were collected at 0 H (48 H after transfection), 24 H, 48 H, and 72 H, respectively. Immunoreactive signals were revealed using the ECL methods and visualized in an IS4000MM Digital Imaging System (Eastman Kodak, Rochester, N.Y.).

Experimental Results.

Figure 4:
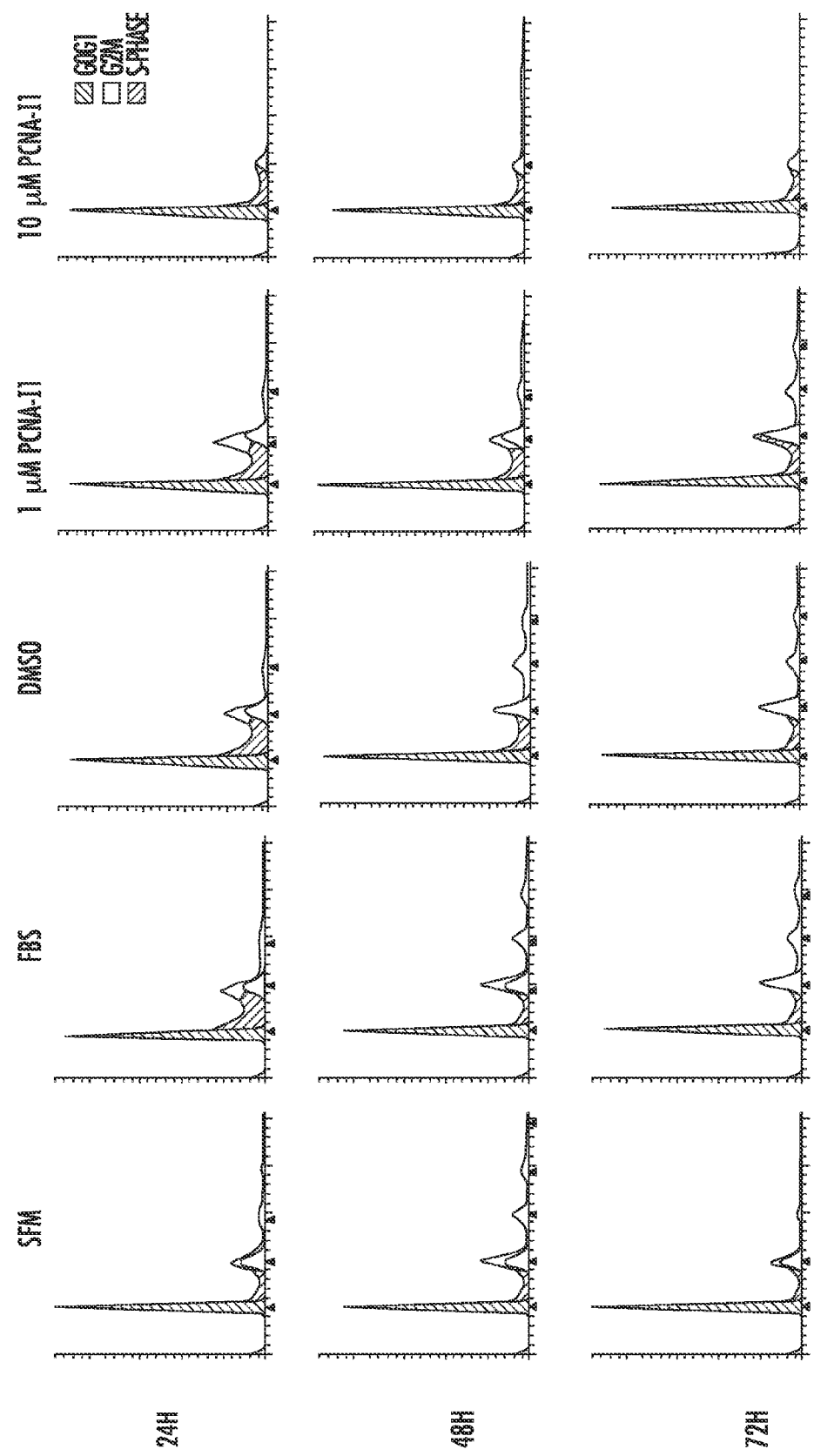
FIG. 4 is a cell cycle distribution profile of PC-3 cells in serum free medium (SFM) or in medium supplemented with 5% FBS in the absence or presence of PCNA-I1 (1 µM) at 24 H, 48 H, and 72 H.
Figure 5:
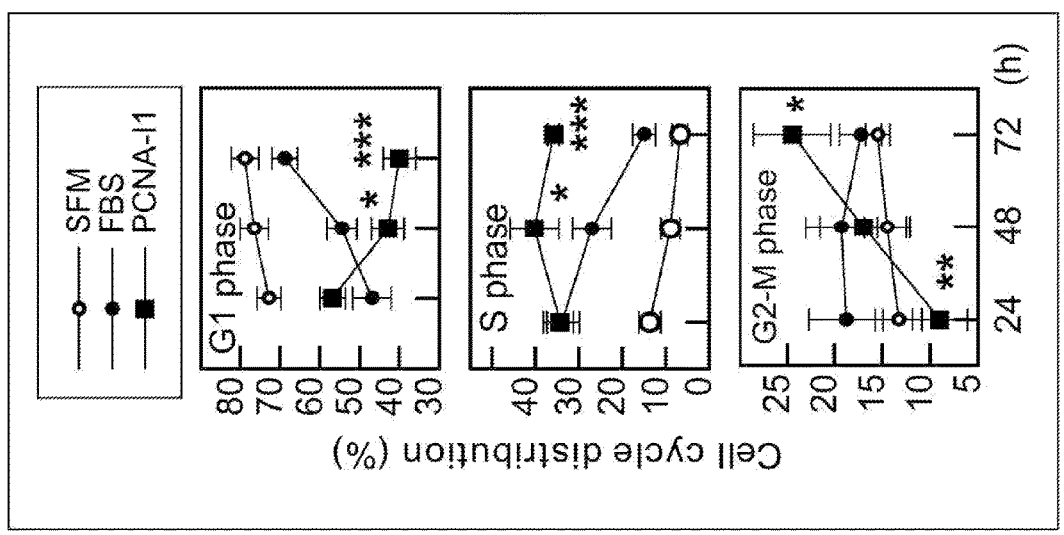
FIG. 5 is a cell cycle distribution profile of PC-3 cells in serum free medium (SFM) or in medium supplemented with 5% FBS in the absence or presence of PCNA-I1 (1 µM) in the G1 phase, S phase, and G2-M phase of the cell cycle at 24 H, 48 H, and 72 H.

Referring to FIGS. 4 and 5, serum starvation led to accumulation of cells in G1 phase of the cell cycle at all times examined. The G1 arrest was rescued upon serum stimulation with the fraction of cells in G1 phase significantly reduced in the first 24 H. With the cell cycle progression, population of cells in G1 phase increased thereafter. By 72 H, the number of cells in G1 phase was close to the culture without serum stimulation. Upon serum stimulation, the number of cells in S phase increased significantly in the first 24 H and then decreased to a value close to the basal level by 72 H. Similarly, the number of cells in the G2/M phase increased in the first 24 H and reduced at 48 H and 72 H.

A significantly different cell distribution profile was noted in cultures treated with PCNA-I1, which partially attenuated the serum-stimulated G1 decrease at 24 H but led to significant G1 reductions at 48 H and 72 H. Additionally, the number of cells in S phase significantly increased at 24 H in cultures treated with PCNA-I1, and, unlike the culture stimulated with serum alone, the distribution of cells in S phase remained high at 48 H and 72H. Upon treatment with PCNA-I1, fewer cells progressed into G2/M phase during the first 24 H, due to the accumulation of cells in G1 and S phases. The G2/M fraction of cells in PCNA-I1 treated cultures, however, increased steadily at 48 H and 72 H. The similar S and G2/M arrest was also observed in cells treated with other PCNA inhibitors at concentrations equivalent to about three to five times of the $IC_{50}$ values (data not shown). Therefore, the cell cycle distribution analysis indicated that treatment with PCNA inhibitors led to a moderate G1 phase accumulation during the first 24 H and an S and G2/M phase arrest at 72 H.

Figure 6:
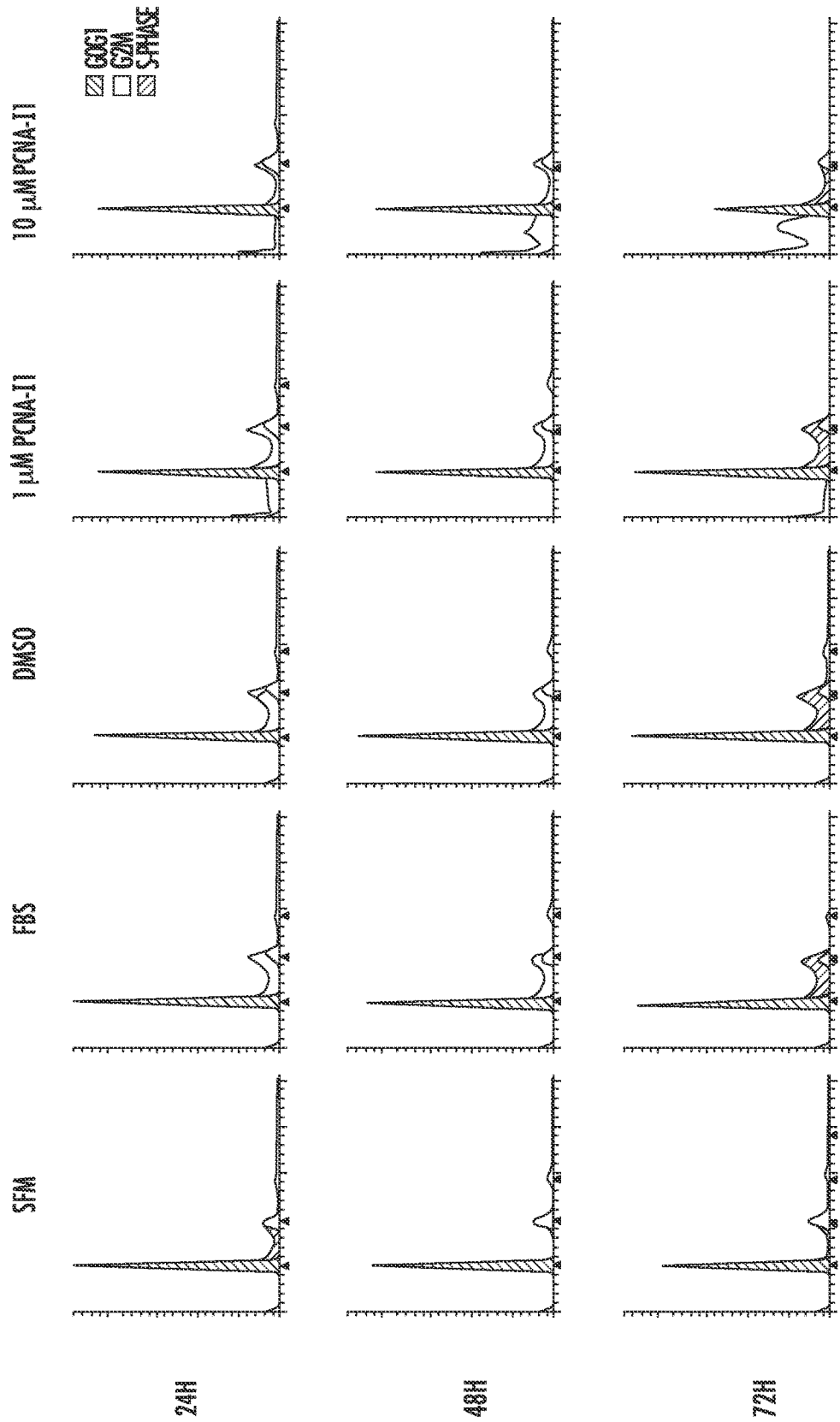
FIG. 6 is a cell cycle distribution profile of PC-3 cells in serum free medium (SFM) or in medium supplemented with 5% FBS in the absence or presence of control scrambled siRNA (200 pmol) or PCNA-siRNA (200 pmol) at 24 H, 48 H, and 72 H.
Figure 7:
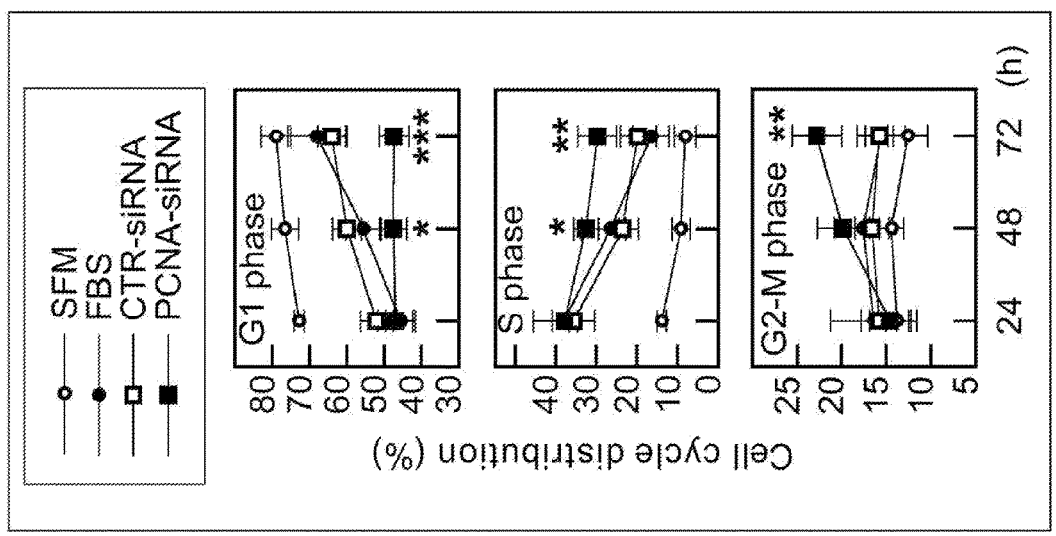
FIG. 7 is a cell cycle distribution profile of PC-3 cells in serum free medium (SFM) or in medium supplemented with 5% FBS in the absence or presence of control scrambled siRNA (200 pmol) or PCNA-siRNA (200 pmol) in the G1 phase, S phase, and G2-M phase of the cell cycle at 24 H, 48 H, and 72 H.

As shown in FIGS. 6 and 7, the transfection of PCNA specific siRNA, but not the control scrambled siRNA, led to an accumulation of cells in S and G2/M phases of the cell cycle over the 72 H time period, mimicking the effects of the treatment with PCNA-I1. Without being bound by the theory, while the moderate G1 phase accumulation induced by PCNA-I1 was not observed, this was due possibly to the timing of the sampling (72 H after the transfection).

Figure 8:
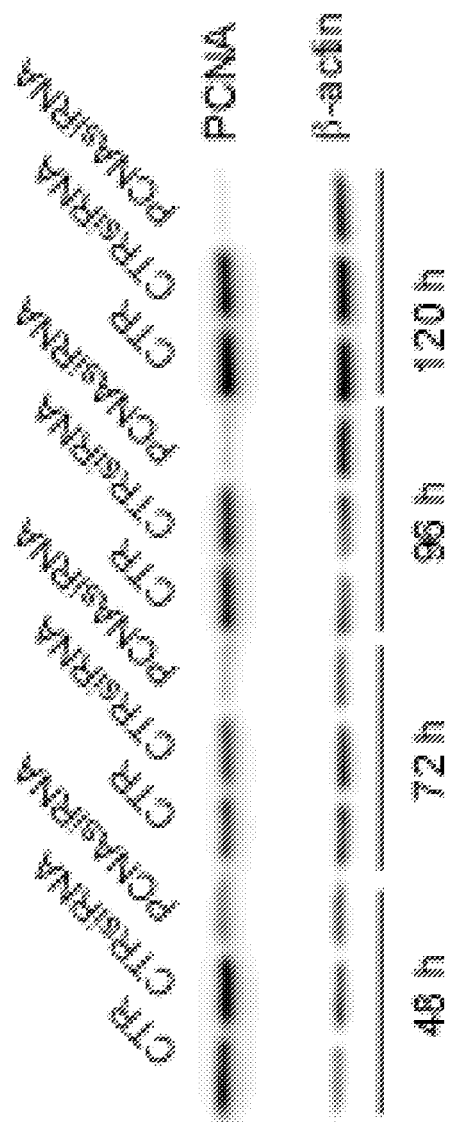
FIG. 8 is a western blot which depicts the expression of PCNA in PC-3 cells transfected with control scrambled siRNA (200 pmol) or PCNA-siRNA (200 pmol) at 48 H, 72 H, and 96 H after transfection.

As shown in FIG. 8, expression of PCNA in cells transfected with PCNA-specific siRNA, but not the scrambled control siRNA, was significantly reduced. A densitometry analysis indicated that the PCNA protein level in PCNA-siRNA transfected cells reduced by 50% at 0 H (48 H after the transfection), 50% at 24 H (the first time point of sampling for the flow cytometry analysis and 72 H after the transfection), 60% at 48 H, and 80% at 72 H, respectively. These data suggest that the S and G2/M arrest induced by the PCNA inhibitors is indeed caused by their interference with PCNA function.

Example 6: Effects of PCNA-I1, PCNA-I2, PCNA-I3, PCNA-I4, PCNA-I6, PCNA-I7, PCNA-I8, PCNA-I9, and PCNA-I10 on PCNA Trimer Formation Experimental Protocol.
The effect of PCNA-I1, PCNA-I2, PCNA-I3, PCNA-I4, PCNA-I6, PCNA-I7, PCNA-I8, PCNA-I9, and PCNA-I10 on PCNA trimer formation was investigated by SDS-PAGE and immunoblotting. Specifically, a trimer formation assay was performed on both PC-3 cell lysates and purified recombinant protein. The trimer formation assay was performed on purified recombinant protein to determine whether the effects of PCNA compounds on the stable trimer formation required the participation of other cellular proteins.

Purified His-PCNA (0.1 µg/reaction) and PC-3 cell lysates (50 µg/reaction) were incubated for 3 H at room temperature in a reaction buffer (40 mM Tris-HCl, pH 7.5, 0.2 mg/mL BSA, 10 mM $MgCl_2$, and 10% glycerol) in the absence or presence of DMSO (0.1% vehicle control) or PCNA-I1, PCNA-I2, PCNA-I3, PCNA-I4, PCNA-I6, PCNA-I7, PCNA-I8, PCNA-I9, or PCNA-I10 (1 µM or 10 µM). The reaction was stopped by addition of the SDS-PAGE sample buffer without a reducing agent. The samples were resolved in SDS-PAGE without boiling and analyzed by immunoblotting using PCNA antibody.

As a control, it was determined whether PCNA inhibitors could induce stable trimers by other cellular proteins. The 9-1-1 protein complex (approximately 110 kD), another member of the clamp family proteins, is a heterotrimer formed by Rad9, Rad1, and Hus1. The 9-1-1 protein complex also encircles DNA and is involved in DNA repair. The PC-3 cell lysate was subjected to the same treatment with 1 or 10 µM of PCNA inhibitors and analyzed for formation of the 9-1-1 protein heterotrimer using an antibody against Hus1.

Figure 9:
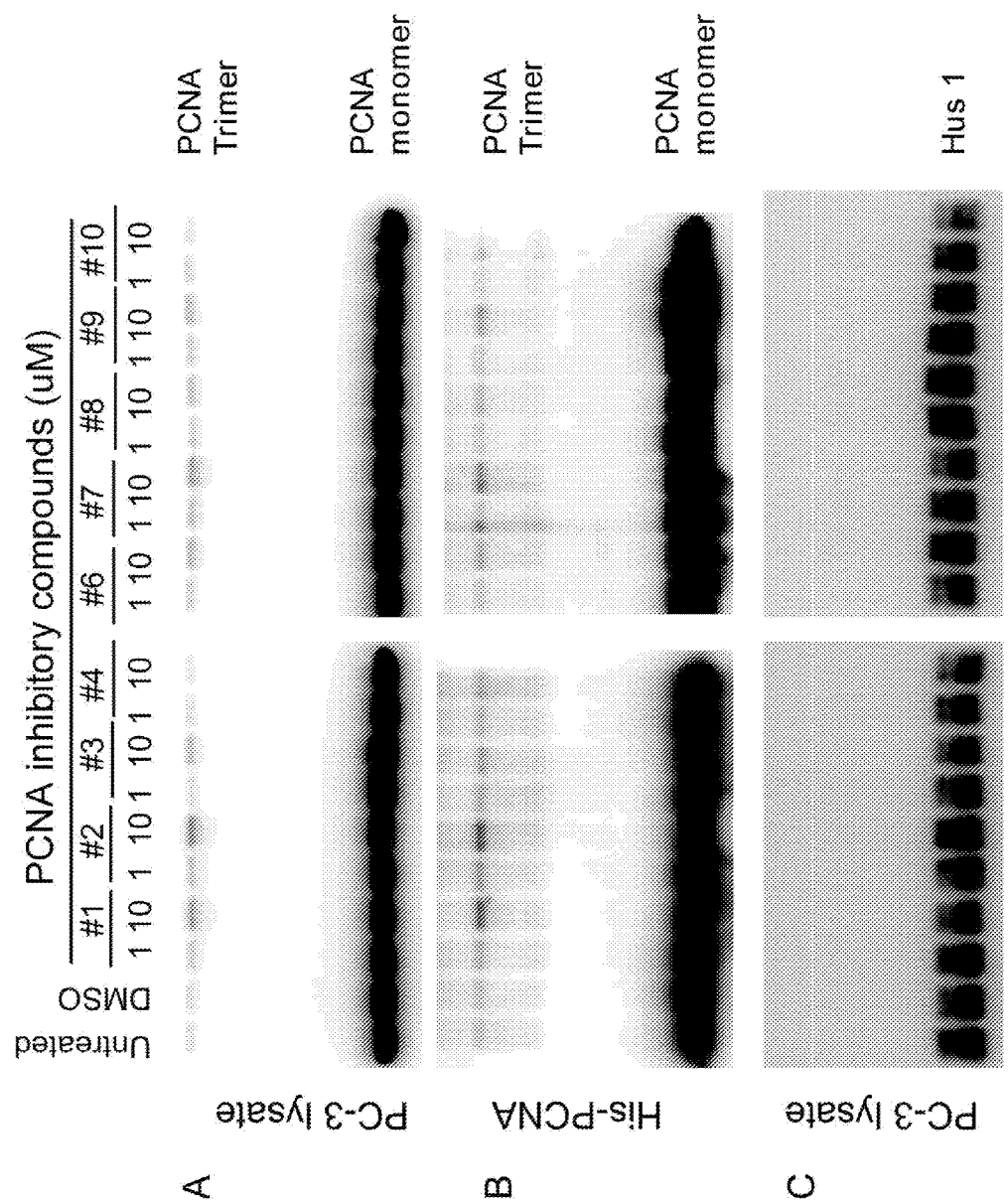
FIG. 9 is an immunoblot which depicts (A) PC-3 lysate, (B) His-PCNA, and (C) PC-3 lysate untreated, in the presence of DMSO, and in the presence or absence of PCNA inhibitory compounds (1 µM or 10 µM)

Experimental Results.
As shown in FIG. 9(A), approximately 1 to 2% of PCNA was present as the trimer form under the experimental conditions. After the incubation with PCNA inhibitors, PCNA-I1 and PCNA-I2 in particular, the portion of PCNA in the trimer form was significantly elevated. Moreover, this effect of the compounds correlated directly with the potency of their inhibitory effects on cell growth. As shown in FIG. 9(B), PCNA inhibitors also caused SDS-refractory stable PCNA trimer formation by the recombinant protein with the same potencies as those observed in the experiment using the PC-3 cell lysate. As shown in FIG. 9(C), a high level of Hus1 was detected in the PC-3 cell lysate. However, the same treatment with PCNA inhibitors did not induce detectable 9-1-1 trimers.

Example 7: Effects of PCNA-I1 on the Association of PCNA with Chromatin

Experimental Protocol.
The encircling of DNA and association with chromatin is required for PCNA to execute its function. Therefore, the effect of PCNA-I1 on the association of PCNA with chromatin was investigated. PC-3 cells were treated for various times with 0.5 µM of PCNA-I1 and lysed in buffer A (10 mM Tris-HCl, pH 7.4, 2.5 mM $MgCl_2$, 0.5% NP-40, 1 mM DTT, 1 mM PMSF, and protease inhibitor cocktail). Samples were pelleted by centrifuge (1500×g, 2 min, 4° C.), and supernatant collected as NP-40-extractable (NP-3) fraction. The pellet was washed in NP-40 buffer B (10 mM Tris-HCl, pH 7.4, 150 mM NaCl, 1 mM PMSF, and a protease inhibitor cocktail) to release the free form of PCNA. The cells were resuspended and digested in buffer C (10 mM Tris-HCl, pH 7.4, 10 mM NaCl, 5 mM $MgCl_2$, 0.2 mM PMSF, and protease inhibitors) with 200 units/$10^7$ cells of DNase I for 30 min at 37° C. After centrifugation at 13,000×g for 5 min at 4° C., the supernatant was collected and fractions were analyzed by western blotting. MCF-7, HeLa, and LNCaP cells were also subjected to treatment with 0.5 µM of PCNA-I1 and subjected to western blotting as previously discussed.

Additionally, PC-3 cells were transfected for 24 H with pGFP-PCNA. The cells were then treated for 4 H with 0.5 µM of PCNA-I1 or 2 µM of PCNA-I2. The intact GFP-PCNA expressing cells were observed under a fluorescent microscope and recorded. After treatment with a buffer with 0.5% NP-40 buffer B, the cells were examined and recorded.

Experimental Results.
As shown in FIG. 10(A), PCNA in the NP-E (NP-40 extractable) and NP-R (NP-40 extraction resistant) fractions were analyzed by immunoblotting with α-tubulin and histone 1 as loading controls to identify the free form of PCNA and the chromatin-associated form of PCNA with α-tubulin and histone 1 as the free form fraction and chromatin-associated form fraction loading controls, respectively. PCNA in NP-E fraction (the free-form PCNA) was not significantly altered in cells treated by PCNA-I1 for up to 8 H but reduced in cells treated for 16 H. In contrast, the level of PCNA in NP-R fraction (the chromatin-associated PCNA) was reduced in 1 to 2 H in cells treated with PCNA-I1. More remarkable reduction of the chromatin-associated PCNA was observed in cells treated with PCNA-I1 for 8 H. Therefore, the reduction of the chromatin-associated PCNA occurred much earlier than did the free form PCNA. As shown in FIG. 10(B), treatment with PCNA-I1 at concentration of 0.5 µM or lower mainly reduced the level of chromatin-associated PCNA and at concentration of 1 µM or higher led to a reduction of both the chromatin-associated and free form PCNA. As shown in FIG. 10(C), a similar reduction of chromatin-associated PCNA by PCNA-I1 was also observed in other cell lines examined, including LNCap, Hela, and A375 cells.

As shown in FIG. 11, nuclear localization of GFP-PCNA was achieved in the control cells. While the treatment of PCNA-I1 and PCNA-I2 did not significantly alter the total intensity of GFP-PCNA, PCNA-I1 and PCNA-I2 reduced the level of chromatin-associated GFP-PCNA.

Example 8: Effects of PCNA-I1 on the Level of Euchromatin- and Heterochromatin-Associated PCNA Experimental Protocol.
Differential effects of PCNA-I1 on the level of euchromatin- (often under active gene transcription) and heterchromatin (often under limited gene transcription) associated PCNA were also investigated. Specifically, PC-3 cells were treated for 8 H with 0.5 µM of PCNA-I1 and PCNA was extracted by procedures known in the art with a combination of limited digestion with micrococcal nuclease and treatment with EDTA to obtain total (S1), euchromatin-associated (S2), and heterochromatin-associated (S3). The extracts were subjected to western blotting analysis.

Experimental Results.
As shown in FIG. 12, PCNA-I1 reduced both euchromatin- and heterochromatin protein 1α (which is associated with both euchromatin and heterochromatin).

Example 9: Effects of PCNA-I1 on the Association of p21Waf1/Cip1 to PCNA

Experimental Protocol.
Chromatin-associated trimeric PCNA executes its function through numerous partner proteins, including p21Waf1/Cip1. To validate that treatment with PCNA-I1 reduces function of PCNA, the binding of p21Waf1/Cip1 to PCNA was investigated. Specifically, Pc-3 and LNCaP cells were treated with PCNA-I1 (0.5 µM) for 8 H and lysed in buffer B as previously discussed. Chromatin-associated protein was extracted in buffer D containing 0.42 M NaCl. The chromatin-associated protein was precipitated with the antibody to PCNA, and was resolved in SDS-PAGE, and probed with antibodies to p21Waf1/Cip1 and PCNA.

Experimental Results.
As shown in FIG. 13, treatment with PCNA-I1 reduced the level of PCNA and p21Waf1/Cip1 in both Pc-3 and LNCaP. Without being bound by the theory, these data indicated that the reduction of DNA-associated PCNA by PCNA-I1 led to a decrease of p21Waf1/Cip1 association with chromatin.

Example 10: Effects of PCNA-I1 on PCNA Stability and Degradation

Experimental Protocol.
PCNA is a very stable protein with a half life of 20 H in replicating cells. The effect of PCNA-I1 on PCNA stability and degradation was investigated. Specifically, PC-3 cells were treated for various times up to 24 H with protein synthesis inhibitor cycloheximide (CHX) to block de novo protein synthesis. Cells were lyzed in buffer A as discussed above and analyzed by immunoblotting. Additionally, because PCNA is subject to ubiquitination regulation, the effect of PCNA-I1 on and deregulation of PCNA through the proteosome-mediated system was also investigated. Specifically, PC-3 cells were treated for 16 H with 0.5 µM PCNA-I1 in the absence or presence of 5 µg/mL of CHX and/or 10 µM of MG132, a well-documented proteosome inhibitor.

Experimental Results.
As shown in FIG. 14(A), PCNA was quite stable and treatment with PC-3 cells for various times up to 24 H with CHX did not significantly alter total PCNA protein level in cells. Additionally, as shown in FIG. 14(B), the total PCNA level was not changed in PC-3 cells exposed to 8 H or 16 H, the times when DNA-associated PCNA was significantly reduced in the absence or presence of CHX. Finally, as shown in FIG. 14(C), the treatments of PCNA-I1, CHX, and MG132, either alone or in all combinations, did not alter the total PCNA protein level in PC-3. In contrast, the level of hsp70, a protein that is degraded through proteosome system, is significantly elevated in cells treated with MG132, indicating that MG132 was effective. Accordingly, PCNA was quite stable and intracellular PCNA levels were not controlled at posttranslational levels by the proteosome-mediated degradation. These data also revealed that PCNA-I1 did not alter PCNA degradation.

Example 11: Differential Effects of PCNA-I1 on Two Different Human Prostate Cancer Cell Lines Experimental Protocol.
Fluorescence-activated cell sorting (FACS) analysis was performed on both PC-3 cells and LNCaP cells using PCNA-I1. Specifically, cells were treated with 1 or 10 µM PCNA-I1 and sampled for the flow cytometry analysis at 24 H, 48 H, and 72 H. Expression of DNA damage and apoptosis-related proteins in PC-3 cells and LNCaP cells was also determined. Cisplatin, a well-known drug that induces DNA damage and apoptosis, was included in the experiment. LNCaP cells were treated for 6 H, 12 H, or 18 H with 10 µM PCNA-I1, 10 µM cisplatin, or both.

To further explore the differential effects of PCNA-I1 on LNCaP and PC-3 cells, the effects of PCNA-I1 and cisplatin on expression of cell cycle- and apoptosis-related proteins in the two cell lines were compared. LNCaP cells and PC-3 cells were treated with 1 µM PCNA-I1 and/or 5 µM cisplatin for 12 H, 18 H, or 24 H and cell lysates were sampled for immunoblotting.

Experimental Results.
As shown in FIG. 15, treatment with lower concentration (1 µM) of PCNA-I1 led to cell growth arrest at S and G2/M phases. At the higher concentration (10 µM), PCNA-I1 caused more significant G1 arrest in PC-3 cells. Apoptosis was not observed in PC-3 cells treated with PCNA-I1 at any concentration and time. In contrast, as shown in FIG. 16, PCNA-I1 treatment, particularly at the higher concentration (10 μM), induced significant apoptosis in LNCaP Cells, reflected in the presence of sub-G1 population of cells in the FACS profile.

As shown in FIG. 17(A), a treatment with PCNA-I1 and cisplatin alone induced moderate double strand break (DSB) of DNA, reflected in induction of γH2AX by the treatment. Synergistic effects on γH2AX induction were observed in cells treated with PCNA-I1 and cisplatin together. Without being bound by the theory, the potential underlying mechanism was that cisplatin-induced DSB could not be efficiently repaired due to the presence of PCNA-I1, which reduced the association of PCNA to chromatin for DNA repair. Cleavage of caspase 3 and poly ADP ribose polymerase (PARP) is a hallmark for the presence of apoptosis. As shown in FIG. 16(B), a treatment with PCNA-I1 or cisplatin alone induced PARP cleavage. Moreover, consistent with induction of DSB (reflected in γH2AX), synergistic effects on PARP cleavage were observed in cells treated with PCNA-I1 and cisplatin. Phosphorylation of p53, which stabilize the protein, was induced by both PCNA-I1 and cisplatin. Additive effects on p53 phosphorylation were observed in cells treated with PCNA-I1 and cisplatin. Furthermore, the treatment with the PCNA-I1 and/or cisplatin also enhanced expression of p21 protein at 6 H and 12 H, which is a p53 target gene and plays an important role in cell cycle and apoptosis regulation.

As shown in FIGS. 17 and 18, treatment with PCNA-I1 and/or cisplatin moderately downregulated expression of cell cycle-regulating proteins, such as retinoblastoma (Rb) and cyclin D1. In contrast, the synergistic effects of PCNA-I1 and cisplatin on expression of γH2AX and cleavaged PARP were observed only in LNCaP cells, which was consistent with differential effects of PCNA-I1 on apoptosis in the two cell lines.

Example 12: Therapeutic Effects of PCNA-I1 in Animal Tumor Models

Experimental Protocols.

The therapeutic effects of PCNA-I1 were evaluated in LNCaP cells and 22Rv1 tumor models. LNCaP or 22Rv1 cells (1-2×10$^6$ cells in gelfoam) were implanted into the subcutis of male nude mice. From four to five days later, tumor-bearing mice were intraperitoneally injected with 10 mg/kg or 50 mg/kg of PCNA-I1. The therapy was continued at three times/week until termination of experiments. Control and treated tumor-bearing mice were monitored daily. Mouse body weight was recorded for toxicity evaluation twice a week and tumor size was measured using calipers twice a week. The experiments were terminated when mice in control groups were moribund. Additionally, to further evaluate potential liver and renal toxicity of PCNA-I1, the blood of tumor-bearing mice were sampled after the treatment with PCNA-I1 for 8 weeks.

Experimental Results.

As shown in FIGS. 20 and 21, the therapy retarded tumor growth in both tumor models. Moreover, the therapy with 50 mg/kg of PCNA-I1 led to eradication of LNCaP tumors in some mice. The actual tumor weights are shown in FIG. 16. Clearly, PCNA-I1 was very effective in this single therapy in both models. Additionally, as shown in FIG. 16, the treatment with 10 or 50 mg/kg of PCNA-I1 (i.p. injection every other day) for up to 8 weeks did not cause significant reduction in the body weight of tumor-bearing mice.

Moreover, as shown in FIG. 21, serum alanine transaminase (ALT or SGPT), aspartate transaminase (AST or SGOT), and blood urea nitrogen (BUN) were not significantly altered by the treatment of PCNA-I1. Accordingly, while not wishing to be bound by the theory, the data suggests that the therapy did not cause apparent system toxic side effects in tumor-bearing mice. Additionally, as shown in FIG. 22, PCNA-I1 therapy reduced PCNA expression in tumor-bearing mice.

Example 13: Effects of PCNA-I1 in Combination with Cisplatin on Cell Growth

Experimental Protocol.

LNCaP or PC-3 cells were treated with a variety of concentrations of PCNA-I1 (0.1-10 μM) or cisplatin (0.1-10 μM) alone, or with a variety of concentrations of a combination of PCNA-I1 (0.1-10 μM) and cisplatin (0.1-10 μM) for four days. MTT assays were performed and IC$_{50}$ values for PCNA-I1 and cisplatin were determined.

Experimental Results.

For LNCaP cells treated with PCNA-I1 alone and cisplatin alone, IC$_{50}$ doses for cell growth inhibition were 0.23 μM (PCNA-I1) and 0.65 μM (cisplatin). For LNCaP cells treated with a combination of PCNA-I1 and cisplatin, 50% inhibition was achieved when LNCaP cells were treated with 0.067 μM PCNA-I1 and 0.3 μM cisplatin.

For PC-3 cells treated with PCNA-I1 alone and cisplatin alone, IC$_{50}$ doses for cell growth inhibition were 0.24 μM (PCNA-I1) and 0.45 μM (cisplatin). For PC-3 cells treated with a combination of PCNA-I1 and cisplatin, 50% inhibition was achieved when PC-3 cells were treated with 0.08 μM PCNA-I1 and 0.3 μM cisplatin.

It is noted that terms like "preferably," "generally," "commonly," and "typically" are not utilized herein to limit the scope of the claims or to imply that certain features are critical, essential, or even important to the structure or function of the claims. Rather, these terms are merely intended to highlight alternative or additional features that may or may not be utilized in a particular embodiment of the present disclosure.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are incorporated herein by reference; the citation of any document is not to be construed as an admission that it is prior art with respect to the present disclosure.

While particular embodiments of the present disclosure have been illustrated and described, it would be obvious to one skilled in the art that various other changes and modifications can be made without departing from the spirit and scope of the disclosure. It is therefore intended to cover in the appended claims all such changes and modifications that are within the scope of this disclosure.

The invention claimed is:

1. A method for inhibiting growth of a cell, the method comprising contacting the cell with an effective amount of a compound structurally depicted as,

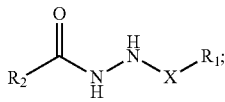

Formula (I)

wherein:
X is

R1 is

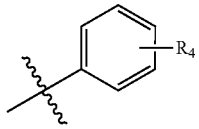

each $R_4$ is independently selected from the group consisting of H, halo, cyano, hydroxyl, and methyl;
$R_2$ is

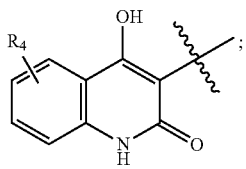

and tautomers thereof, with the proviso that
at least one $R_4$ is not H, and $R_4$ on $R_1$ is neither ortho-halo nor methyl; and
wherein the compound is provided in a concentration of from about 0.1 to about 10 μM, and the growth of the cell is inhibited by up to about 100%.

2. The method according to claim 1, wherein the growth of the cell is inhibited by about 50%.

3. The method according to claim 1, wherein contacting the cell with the compound induces apoptosis of the cell.

4. The method according to claim 1, wherein the cell is a mammalian cell selected from the group consisting of a human cell, a non-human primate cell, a canine cell, a feline cell, a murine cell, a bovine cell, an equine cell, a porcine cell, and a lagomorph cell.

5. The method according to claim 1, wherein the cell is selected from the group consisting of a tumor cell and normal cell, and wherein:
the tumor cell is selected from the group consisting of a breast cancer cell, a prostate cancer cell, a colon cancer cell, a cervical cancer cell, a melanoma cell, a multi-drug resistant colon cancer cell, and a fibrosarcoma cell, and
the normal cell is selected from the group consisting of a blood vessel endothelial cell, a bone marrow mesenchymal stem cell, a mammary epithelial cell, a prostate epithelial cell, a spleen lymphocyte, a lung endothelial cell, and a prostate endothelial cell.

6. The method according to claim 1, wherein the compound is selected from the group consisting of:

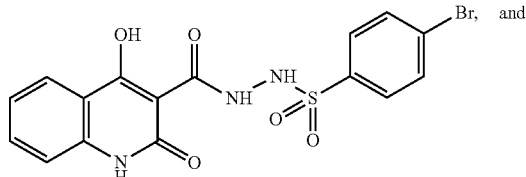

and

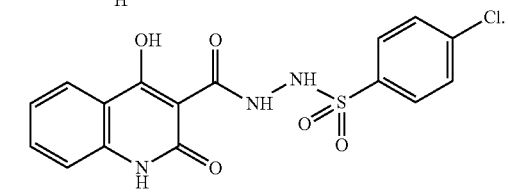

7. The method according to claim 1, further comprising contacting the cell with an effective amount of cisplatin.

8. A method for treating prostate cancer in a subject in need thereof, the method comprising administering an effective amount of a compound to the subject, wherein the compound is depicted structurally as,

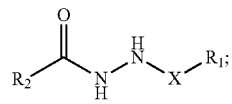

Formula (I)

wherein:
X is

R1 is

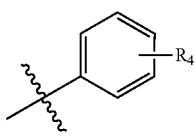

each R$_4$ is independently selected from the group consisting of H, halo, cyano, hydroxyl, and methyl;
R$_2$ is

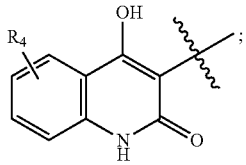

and tautomers thereof, with the proviso that
at least one R$_4$ is not H, and R$_4$ on R$_1$ is neither ortho-halo nor methyl; and
wherein the compound is administered in a dose of about 10 to about 50 µg/g.

9. The method according to claim 8, wherein growth of a prostate tumor is reduced.

10. The method according to claim 9, wherein volume of the prostate tumor is reduced by from about 70% to about 90%.

11. The method according to claim 10, wherein the volume of the prostate tumor is reduced by from about 70% to about 85%.

12. The method according to claim 8, wherein a prostate tumor is eradicated.

13. The method according to claim 8, wherein the compound is administered in a dose of about 10 µg/g every other day.

14. The method according to claim 13, wherein the dose of the compound is systemically administered about three times per week.

15. The method according to claim 8, wherein the subject is a mammal.

16. The method according to claim 15, wherein the mammal is human.

17. The method according to claim 8, wherein the compound is selected from the group consisting of:

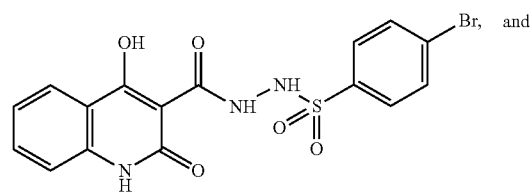

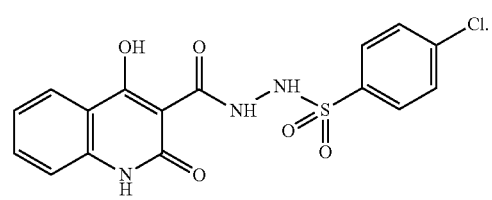

18. A method for inhibiting growth of a cell, the method comprising:
contacting the cell with an effective amount of cisplatin; and
contacting the cell with an effective amount of a compound structurally depicted as,

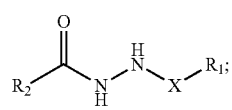

Formula (I)

wherein:
X is

R1 is

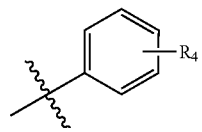

each R$_4$ is independently selected from the group consisting of H, halo, cyano, hydroxyl,
R$_2$ is

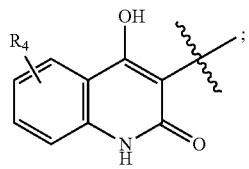

and tautomers thereof, with the proviso that
at least one R$_4$ is not H, and R$_4$ on R$_1$ is neither ortho-halo nor methyl.

19. The method according to claim 18, wherein the growth of the cell is inhibited by up to about 100%.

20. The method according to claim 18, wherein the growth of the cell is inhibited by about 50%.

21. The method according to claim 18, wherein the compound is provided in a concentration of from about 0.1 to about 10 µM.

22. The method according to claim 18, wherein contacting the cell with the compound induces apoptosis of the cell.

23. The method according to claim 18, wherein the cell is a mammalian cell selected from the group consisting of a human cell, a non-human primate cell, a canine cell, a feline cell, a murine cell, a bovine cell, an equine cell, a porcine cell, and a lagomorph cell.

24. The method according to claim 18, wherein the cell is selected from the group consisting of a tumor cell and normal cell, and wherein:
the tumor cell is selected from the group consisting of a breast cancer cell, a prostate cancer cell, a colon cancer cell, a cervical cancer cell, a melanoma cell, a multi-drug resistant colon cancer cell, and a fibrosarcoma cell, and
the normal cell is selected from the group consisting of a blood vessel endothelial cell, a bone marrow mesenchymal stem cell, a mammary epithelial cell, a prostate epithelial cell, a spleen lymphocyte, a lung endothelial cell, and a prostate endothelial cell.

25. The method according to claim 18, wherein the compound is selected from the group consisting of:

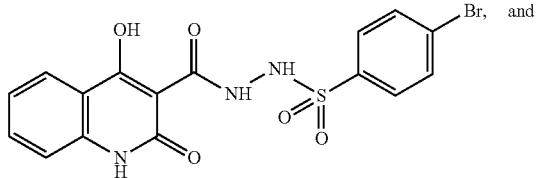

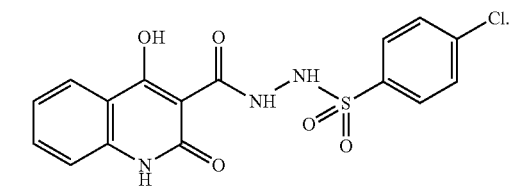

26. A method for treating prostate cancer in a subject in need thereof, the method comprising administering an effective amount of a compound to the subject, wherein the compound is selected from the group consisting of:

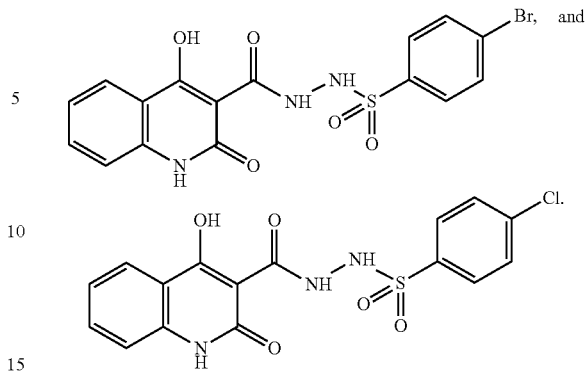

27. The method according to claim 26, wherein the compound is administered in a dose of about 10 to about 50 µg/g.

28. The method according to claim 27, wherein the compound is administered in a dose of about 10 µg/g every other day.

29. The method according to claim 27, wherein the dose of the compound is systemically administered about three times per week.

30. The method according to claim 26, wherein the subject is a mammal.

31. The method according to claim 30, wherein the mammal is human.

* * * * *